United States Patent
Yamada et al.

(10) Patent No.: US 12,319,891 B2
(45) Date of Patent: Jun. 3, 2025

(54) METHOD FOR RELEASING ALDEHYDE OR KETONE

(71) Applicant: TAKASAGO INTERNATIONAL CORPORATION, Tokyo (JP)

(72) Inventors: Shinya Yamada, Kanagawa (JP); Tadahide Hatakeyama, Kanagawa (JP); Takahiro Ishikawa, Kanagawa (JP); Masato Murai, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 1011 days.

(21) Appl. No.: 17/359,744

(22) Filed: Jun. 28, 2021

(65) Prior Publication Data

US 2021/0348081 A1    Nov. 11, 2021

Related U.S. Application Data

(62) Division of application No. 16/477,644, filed as application No. PCT/JP2018/001676 on Jan. 19, 2018, now abandoned.

(30) Foreign Application Priority Data

Jan. 19, 2017    (JP) ................................. 2017-007930
Mar. 23, 2017    (JP) ................................. 2017-058118

(51) Int. Cl.
| | | |
|---|---|---|
| *A61K 8/368* | (2006.01) | |
| *A61L 9/01* | (2006.01) | |
| *A61L 9/04* | (2006.01) | |
| *A61Q 5/02* | (2006.01) | |
| *A61Q 5/12* | (2006.01) | |
| *C07C 69/78* | (2006.01) | |
| *C11B 9/00* | (2006.01) | |
| *C11D 3/50* | (2006.01) | |
| *C12P 7/24* | (2006.01) | |
| *C12P 7/26* | (2006.01) | |

(52) U.S. Cl.
CPC ............ *C11B 9/0061* (2013.01); *A61K 8/368* (2013.01); *A61L 9/01* (2013.01); *A61L 9/04* (2013.01); *A61Q 5/02* (2013.01); *A61Q 5/12* (2013.01); *C07C 69/78* (2013.01); *C11D 3/50* (2013.01); *C12P 7/24* (2013.01); *C12P 7/26* (2013.01)

(58) Field of Classification Search
CPC .............. C12P 7/26; A61K 8/368; C11B 9/00
See application file for complete search history.

(56) References Cited

U.S. PATENT DOCUMENTS

| | | |
|---|---|---|
| 6,207,857 B1 | 3/2001 | Anderson et al. |
| 6,232,487 B1 | 5/2001 | Anderson et al. |
| 2002/0054893 A1 | 5/2002 | Ishida et al. |
| 2003/0083376 A1 | 5/2003 | Eh et al. |
| 2007/0053860 A1 | 3/2007 | Eh et al. |
| 2008/0269102 A1 | 10/2008 | Flachsmann et al. |
| 2010/0137627 A1 | 6/2010 | Flachsmann et al. |
| 2010/0152264 A1 | 6/2010 | Herrmann et al. |
| 2011/0318289 A1 | 12/2011 | Frodyma et al. |

FOREIGN PATENT DOCUMENTS

| | | |
|---|---|---|
| CN | 101407490 B | 1/2012 |
| EP | 0 387 586 A1 | 9/1990 |
| EP | 0 887 335 A1 | 12/1998 |
| EP | 0 955 035 A1 | 11/1999 |
| EP | 1 285 906 A2 | 2/2003 |
| EP | 3 689 849 A1 | 8/2020 |
| JP | 2-223524 A | 9/1990 |
| JP | 4-337395 A | 11/1992 |

(Continued)

OTHER PUBLICATIONS

Office Action issued Apr. 19, 2022, issued by the Japan Patent Office in counterpart Japanese Patent Application No. 2018-562468.

(Continued)

*Primary Examiner* — Tekchand Saidha
(74) *Attorney, Agent, or Firm* — Sughrue Mion, PLLC

(57) ABSTRACT

A method for releasing an aldehyde or ketone of formula (2) by allowing a hydrolase to act on a compound of formula (1) is disclosed. The compound of formula (1) is used as a flavor or fragrance precursor. In formulas (1) and (2), each of $R^1$, $R^2$ and $R^3$ independently represents a hydrogen atom, an alkyl group which may have a substituent, a cycloalkyl group which may have a substituent, an alkenyl group which may have a substituent, an aryl group which may have a substituent, or an aralkyl group which may have a substituent; $R^1$ and $R^2$ or $R^1$ and $R^3$ may form a ring; Ar represents an aryl group which may have a substituent:

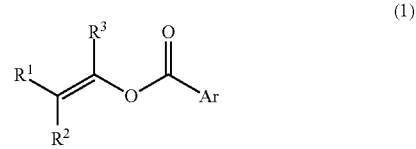

(1)

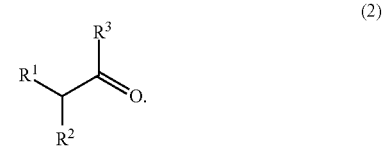

(2)

3 Claims, No Drawings

(56) References Cited

FOREIGN PATENT DOCUMENTS

| | | | |
|---|---|---|---|
| JP | 11-147852 | A | 6/1999 |
| JP | 11-286428 | A | 10/1999 |
| JP | 2001-303090 | A | 10/2001 |
| JP | 2002-88391 | A | 3/2002 |
| JP | 2003-160792 | A | 6/2003 |
| JP | 2004-315502 | A | 11/2004 |
| JP | 2007-509199 | A | 4/2007 |
| JP | 2007-522154 | A | 8/2007 |
| JP | 2009-46442 | A | 3/2009 |
| JP | 2010-527990 | A | 8/2010 |
| JP | 2013-529642 | A | 7/2013 |
| WO | 2005/077881 | A1 | 8/2005 |

OTHER PUBLICATIONS

European Patent Office, Extended European Search Report dated Feb. 22, 2021, issued in counterpart European Patent Application No. 18741889.2.

Herrmann, "Controlled Release of Volatiles under Mild Reaction Conditions: From Nature to Everyday Products," Angewandte Chemie International Edition, Verlag Chemie, vol. 46, Aug. 2007, pp. 5836-5863.

International Search Report (PCT/ISA/210) dated Apr. 24, 2018 issued by the International Searching Authority in International Application No. PCT/JP2018/001676.

Written Opinion (PCT/ISA/237) dated Apr. 24, 2018 issued by the International Searching Authority in International Application No. PCT/JP2018/001676.

Dana P. Simmons et al., "Aldehyde Enol Esters as Novel Chain Terminators in Cationie Olefin Cyclizations", Helvetica Chimica Acta, vol. 71, 1988, pp. 1000-1004.

Michikazu Yoshioka et al., "Photochemical Reaction of Phenyl-substituted 1,3-Diketones", Bulletin of the Chemical Society of Japan, vol. 57, No. 6, Jun. 1984, pp. 1604-1607, 4 pages total, XP055726154.

Communication dated Sep. 7, 2020 issued by the European Intellectual Property Office in counterpart European Application No. 18741889.2.

Slonczewski, J. et al. Microbiology Norton, 2017 p. 904.

Communication dated Oct. 26, 2021 issued by the Japanese Patent Office in application No. 2018-562468.

METHOD FOR RELEASING ALDEHYDE OR KETONE

CROSS REFERENCE TO RELATED APPLICATIONS

This application is a divisional of U.S. patent application Ser. No. 16/477,644, filed Jul. 12, 2019, which is a National Stage of International Application No. PCT/JP2018/001676, filed on Jan. 19, 2018, which claims priority from Japanese Patent Application No. 2017-058118, filed on Mar. 23, 2017, and Japanese Patent Application No. 2017-007930, filed on Jan. 19, 2017, the contents of which are incorporated herein by reference in their entireties.

TECHNICAL FIELD

The present invention relates to a flavor or fragrance precursor which releases an aldehyde or a ketone by the action of hydrolase, a technique for lasting lingering fragrance, and a deodorization technique of releasing, as a deodorizing component, an aldehyde or a ketone by the action of a microorganism and mitigating the odor caused by microorganisms.

BACKGROUND ART

In recent years, with an increased consumer's interest in fragrance, a demand for fragrance at the time of using a product ranges widely. With respect to the needs for improvements in the fragrance substantivity, compounded flavors or fragrances or flavor or fragrance capsules, in which a lot of a last note component with low volatility is blended, are used in general.

In addition, as a fragrance substantivity-enhancing agent, for example, a fixative such as p-menthane-3,8-diol (Patent Literature 1) and 3-(menthoxy)-1,2-propanediol (Patent Literature 2) has been proposed.

On the other hand, in recent years, due to an increased interest in hygiene, many people have become sensitized to "a scent in living space" and consequently, even a scent that they have been heretofore not aware of in life often assumes a target malodor.

Among these, malodors associated with human body or laundry are known to be mainly caused by microorganisms. As the method for deodorizing these malodors, there are used, for example, a method of suppressing proliferation of microorganisms by using an antimicrobial (Patent Literature 3), and a method of alleviating unpleasant sensation by using a flavor or fragrance (Patent Literatures 4 and 5).

Furthermore, the flavor or fragrance is highly useful in that not only an offensive odor is reduced but also a malodor can be changed to a pleasant scent. A flavor or fragrance component such as aldehydes or ketones has an aromaticity and is expected to provide a sensory deodorization effect. Among flavor or fragrance components, particularly, aldehydes have not only a sensuous deodorization effect but also further have a chemical deodorization effect (Patent Literature 6) and therefore, these are expected to provide a higher deodorizing effect.

RELATED ART

Patent Literature

Patent Literature 1: JP-A-4-337395
Patent Literature 2: JP-A-2002-88391
Patent Literature 3: JP-A-2009-46442
Patent Literature 4: JP-A-2004-315502
Patent Literature 5: JP-A-11-286428
Patent Literature 6: JP-A-2001-303090

SUMMARY OF THE INVENTION

Problems that the Invention is to Solve

However, when a compounded flavor or fragrance is used in a product, for example, after clothing or hair is cleaned with a cleaner, most of flavor or fragrance components are washed away into water together with cleaning components such as surfactant and therefore, only a very small amount of flavor or fragrance components remain in clothing or hair.

In addition, many flavor or fragrance components are volatilized in drying step, as a result, the lingering fragrance intensity is reduced. Furthermore, since the lingering fragrance component is disproportionated to a flavor or fragrance component having an extremely low volatility, the taste is readily deteriorated, and an unpleasant taste may be felt.

In the case of using a flavor or fragrance capsule, the lingering fragrance may be enhanced, but there is a problem that stabilization in a product is difficult and the application field is limited; and since a fragrance is not released unless the capsule is physically broken, a fragrance may be emitted when the lingering fragrance is not needed, or a fragrance is not given when the lingering fragrance is needed, causing a gap between the need for a fragrance and the timing of emitting a fragrance from the capsule.

In addition, when a fixative is used as a fragrance substantivity-enhancing agent together with a compounded flavor or fragrance, the lingering fragrance property may be somewhat enhanced, but fully satisfactory substantivity of lingering fragrance has not been obtained.

Furthermore, since the lingering fragrance component is still disproportionated to a low-volatile component, these techniques did not lead to an improvement in the fragrance quality of the lingering fragrance, and a technique for lasting fragrance to allow a flavor or fragrance with fresher feeling to last is demanded.

On the other hand, in the case of using an antimicrobial in a personal care product such as a deodorant agent, not only bacteria causing a malodor but also bacteria useful on skin are killed, and the skin flora balance may be lost. The indigenous skin bacteria also fulfill the role of keeping the pH weakly acidic and preventing skin infections and in view of maintaining the health of the skin, frequent use of an antimicrobial is not necessarily favorable.

In addition, after washing clothing or hair with a cleaner containing an antimicrobial, most of the antimicrobial components are washed away into water together with cleaning components such as surfactant and therefore, only a very small amount of antimicrobial components remain in clothing or hair. In order to kill the malodor-causing bacteria to such an extent that offensive odor is not sensed, a large amount of antimicrobial or an antimicrobial having a high bactericidal effect needs to be used, and this may raise the concern of adverse effect on human body or environment and cause a rise in the cost.

Furthermore, in the case of using a flavor or fragrance as a sensory deodorant, this is effective in the short term, but since the fragrance intensity weakens due to volatilization of a flavor or fragrance component with time, the deodorizing effect does not last. Moreover, as for the malodor caused by microorganisms, the odor intensity and unpleasant sensation are strengthened along with progress of proliferation of microorganisms, and it is likely that when the consumer truly needs the deodorizing effect, a sufficient deodorizing effect is not obtained due to weak lingering fragrance intensity of the flavor or fragrance. The lingering fragrance property may be increased to enhance the sustained deodorization, but since this leads to inclination to a flavor or fragrance component having an extremely low volatility in the flavor or fragrance composition, the taste is readily deteriorated, and discomfort may be felt.

It may also be conceived to use a flavor or fragrance having a high fragrance intensity or extremely raise the perfuming amount, but, for example, at the start of use of a deodorant product, during use of a body cleaner, or during drying of clothing, the flavor or fragrance smells too strong, and the user may be offended.

Accordingly, for the malodor caused by microorganisms, a deodorization technique capable of exerting a deodorizing effect at the same timing as sufficient proliferation of microorganisms and generation of malodor is demanded.

The present invention has been made in consideration of these conventional circumstances, and an object of the present invention is to develop a technique enabling a lingering fragrance having fresh feeling to last.

Another object of the present invention is to develop a deodorizing method and a deodorant, which can exert a deodorizing effect on the malodor caused by microorganisms at the same timing as sufficient proliferation of microorganisms and generation of malodor.

Means for Solving the Problems

As a result of intensive studies to attain the objects above, the present inventors have found that when a compound having a specific structure releases an aromatic aldehyde or ketone by the action of a hydrolase, the substantivity of lingering fragrance having fresh feeling is increased.

In addition, the present inventors have found that when a compound having a specific structure releases an aldehyde or a ketone by the action of a microorganism, the odor caused by microorganisms is alleviated.

More specifically, the present invention relates to the following [1] to [17].

[1] A method for releasing an aldehyde or ketone represented by formula (2) by allowing a hydrolase to act on a compound represented by formula (1), in which the compound represented by formula (1) is used as a flavor or fragrance precursor:

[Chem. 1]

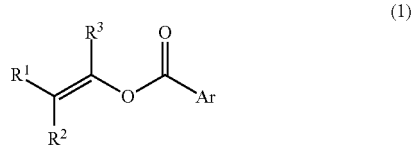

(1)

(in formula (1), each of $R^1$, $R^2$ and $R^3$ independently represents a hydrogen atom, an alkyl group which may have a substituent, a cycloalkyl group which may have a substituent, an alkenyl group which may have a substituent, an aryl group which may have a substituent, or an aralkyl group which may have a substituent, $R^1$ and $R^2$ or $R^1$ and $R^3$ may form a ring, and Ar represents an aryl group which may have a substituent), and:

[Chem. 2]

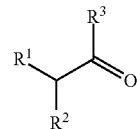

(2)

(in formula (2), $R^1$, $R^2$ and $R^3$ have the same definitions as those in formula (1), and $R^1$ and $R^2$ or $R^1$ and $R^3$ may form a ring).

[2] The method for releasing an aldehyde or a ketone according to [1], wherein the hydrolase is lipase.

[3] The method for releasing an aldehyde or a ketone according to [1] or [2], wherein each of $R^1$, $R^2$ and $R^3$ is independently a hydrogen atom, an alkyl group having 1 to 13 carbon atoms, which may have a substituent, or an alkenyl group having 2 to 13 carbon atoms, which may have a substituent.

[4] A deodorizing method including allowing a microorganism to act on a compound represented by formula (1) to release, as a deodorizing component, an aldehyde or ketone represented by formula (2) and mitigating an odor caused by microorganism:

[Chem. 3]

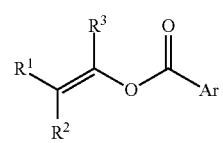

(1)

(in formula (1), each of $R^1$, $R^2$ and $R^3$ independently represents a hydrogen atom, an alkyl group which may have a substituent, a cycloalkyl group which may have a substituent, an alkenyl group which may have a substituent, an aryl group which may have a substituent, or an aralkyl group which may have a substituent, $R^1$ and $R^2$ or $R^1$ and $R^3$ may form a ring, and Ar represents an aryl group which may have a substituent), and:

[Chem. 4]

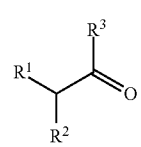

(2)

(in formula (2), $R^1$, $R^2$ and $R^3$ have the same definitions as those in formula (1), and $R^1$ and $R^2$ or $R^1$ and $R^3$ may form a ring).

[5] The deodorizing method according to [4], wherein the microorganism is at least one selected from the group consisting of *Staphylococcus* bacteria, *Corynebacterium* bacteria, *Propionibacterium* bacteria, *Pseudomonas* bacteria, *Bacillus* bacteria, *Moraxella* bacteria, and *Malassezia* fungi.

[6] The deodorizing method according to [4] or [5], wherein each of $R^1$, $R^2$ and $R^3$ is independently a hydrogen atom, an alkyl group having 1 to 13 carbon atoms, which may have a substituent, or an alkenyl group having 2 to 13 carbon atoms, which may have a substituent.

[7] A compound represented by formula (3):

[Chem. 5]

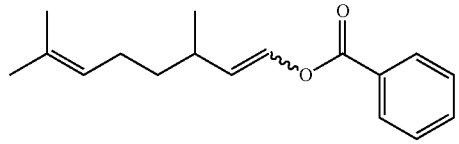

(3)

(in formula (3), a wavy line represents either one of E and Z geometric isomers or a mixture thereof).

[8] A compound represented by formula (4):

[Chem. 6]

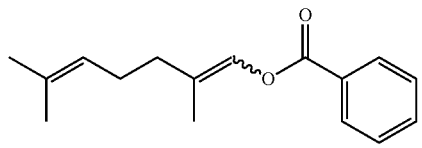

(4)

(in formula (4), a wavy line represents either one of E and Z geometric isomers or a mixture thereof).

[9] A flavor or fragrance composition containing a compound represented by formula (1):

[Chem. 7]

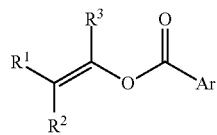

(1)

(in formula (1), each of $R^1$, $R^2$ and $R^3$ independently represents a hydrogen atom, an alkyl group which may have a substituent, a cycloalkyl group which may have a substituent, an alkenyl group which may have a substituent, an aryl group which may have a substituent, or an aralkyl group which may have a substituent, $R^1$ and $R^2$ or $R^1$ and $R^3$ may form a ring, and Ar represents an aryl group which may have a substituent).

[10] The flavor or fragrance composition according to [9], wherein each of $R^1$, $R^2$ and $R^3$ is independently a hydrogen atom, an alkyl group having 1 to 13 carbon atoms, which may have a substituent, or an alkenyl group having 2 to 13 carbon atoms, which may have a substituent.

[11] A flavor or fragrance composition containing a compound represented by formula (3):

[Chem. 8]

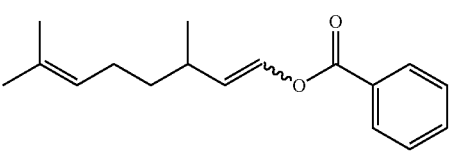

(3)

(in formula (3), a wavy line represents either one of E and Z geometric isomers or a mixture thereof).

[12] A flavor or fragrance composition containing a compound represented by formula (4):

[Chem. 9]

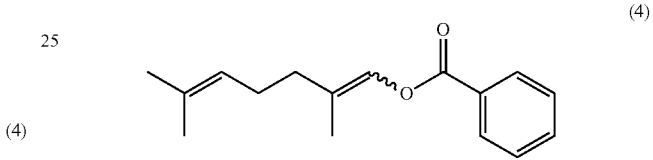

(4)

(in formula (4), a wavy line represents either one of E and Z geometric isomers or a mixture thereof).

[13] An aroma product, a laundry care product, a hair care product, a cosmetic, a cleaner or a deodorant, containing a compound represented by formula (1):

[Chem. 10]

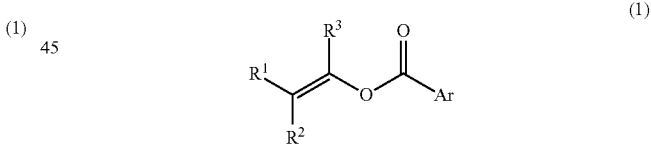

(1)

(in formula (1), each of $R^1$, $R^2$ and $R^3$ independently represents a hydrogen atom, an alkyl group which may have a substituent, a cycloalkyl group which may have a substituent, an alkenyl group which may have a substituent, an aryl group which may have a substituent, or an aralkyl group which may have a substituent, $R^1$ and $R^2$ or $R^1$ and $R^3$ may form a ring, and Ar represents an aryl group which may have a substituent).

[14] The aroma product, laundry care product, hair care product, cosmetic, cleaner or deodorant according to [13], wherein each of $R^1$, $R^2$ and $R^3$ is independently a hydrogen atom, an alkyl group having 1 to 13 carbon atoms, which may have a substituent, or an alkenyl group having 2 to 13 carbon atoms, which may have a substituent.

[15] An aroma product, a laundry care product, a hair care product, a cosmetic, a cleaner or a deodorant, containing a compound represented by formula (3):

[Chem. 11]

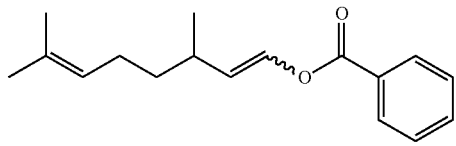

(3)

(in formula (3), a wavy line represents either one of E and Z geometric isomers or a mixture thereof).

[16] An aroma product, a laundry care product, a hair care product, a cosmetic, a cleaner or a deodorant, containing a compound represented by formula (4):

[Chem. 12]

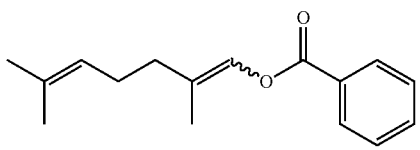

(4)

(in formula (4), a wavy line represents either one of E and Z geometric isomers or a mixture thereof).

[17] An aroma product, a laundry care product, a hair care product, a cosmetic, a cleaner or a deodorant, containing the flavor or fragrance composition according to any one of [9] to [12].

Advantage of the Invention

In the present invention, the compound represented by formula (1) can release an aldehyde or ketone having aromaticity by the action of a hydrolase and increase the substantivity of a lingering fragrance having fresh feeling.

In addition, by incorporating the compound represented by formula (1), a flavor or fragrance composition, an aroma product, a laundry care product, a hair care product, a cosmetic, or a cleaner, each of which emits an aroma when allowing a hydrolysate to act thereon and causes a lingering fragrance having fresh feeling to last, can be provided.

Furthermore, in the present invention, the compound represented by formula (1) can release an aldehyde or ketone having a deodorizing effect, represented by formula (2), by the action of a microorganism and mitigate the odor caused by microorganisms.

Moreover, by incorporating the compound represented by formula (1), a deodorant which can emit a deodorizing component when allowing a microorganism to act thereon and mitigate the offensive odor caused by microorganisms, can be provided.

MODE FOR CARRYING OUT THE INVENTION

The present invention is described in detail below.

In the present invention, a compound represented by formula (1) is used as a flavor or fragrance precursor and by allowing a hydrolysate to act thereon, an aldehyde or a ketone, which is a compound represented by formula (2) as a flavor or fragrance component, can be emitted.

In addition, by allowing a microorganism to act on the compound represented by formula (1), an aldehyde or ketone, which is a deodorizing component represented by formula (2), can be emitted, and this makes it possible to mitigate the odor caused by microorganisms and perform the deodorization.

[Compound Represented by Formula (1) and Compound Represented by Formula (2)]

The compound represented by formula (1) and the compound represented by formula (2) are described.

Compound represented by formula (1):

[Chem. 13]

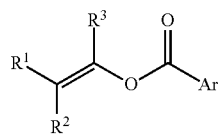

(1)

In formula (1), each of $R^1$, $R^2$ and $R^3$ independently represents a hydrogen atom, an alkyl group which may have a substituent, a cycloalkyl group which may have a substituent, an alkenyl group which may have a substituent, an aryl group which may have a substituent, or an aralkyl group which may have a substituent, $R^1$ and $R^2$ or $R^1$ and $R^3$ may form a ring, and Ar represents an aryl group which may have a substituent.

Compound represented by formula (2):

[Chem. 14]

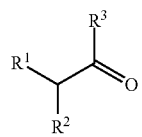

(2)

In formula (2), $R^1$, $R^2$ and $R^3$ have the same definitions as those in formula (1). $R^1$ and $R^2$ or $R^1$ and $R^3$ may form a ring.

(Groups Represented by $R^1$, $R^2$ and $R^3$)

The alkyl group, the cycloalkyl group, the alkenyl group, the aryl group and the aralkyl group, each of which is represented by $R^1$, $R^2$ and $R^3$, are described. Each of these groups may have a substituent.

The alkyl group includes, for example, a straight chain or branched alkyl group having 1 to 30 carbon atoms, preferably 1 to 13 carbon atoms. Specifically, examples thereof include a methyl group, an ethyl group, a n-propyl group, an isopropyl group, a n-butyl group, a 2-butyl group, an isobutyl group, a tert-butyl group, a n-pentyl group, a 2-pentyl group, a 3-pentyl group, a tert-pentyl group, a 2-methylbutyl group, a 3-methylbutyl group, a 2,2-dimethylpropyl group, a 1,2-dimethylpropyl group, a n-hexyl group, a 2-hexyl group, a 3-hexyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a heptyl group, an octyl group, a 1,5-dimethylhexyl group, a nonyl group, a decyl group, an undecyl group, a dodecyl group, a tridecyl group, a 1,5,9-trimethyldecyl group, a tetradecyl group, a pentadecyl group, a hexadecyl group, a heptadecyl group, an octadecyl group, a nonadecyl group, an eicosyl group, a heneicosyl group, a docosyl group, etc.

Examples of the cycloalkyl group include a cyclopropyl group, a cyclobutyl group, a cyclopentyl group, a cyclohexyl group, etc.

The alkenyl group includes, for example, a straight chain or branched alkenyl group having 2 to 20 carbon atoms, preferably 2 to 13 carbon atoms, and a cyclic alkenyl group having 3 to 20 carbon atoms, preferably 5 to 10 carbon atoms.

Specifically, examples of the alkenyl group include a vinyl group, a 1-propenyl group, a 2-propenyl group, a 1-butenyl group, a 2-butenyl group, a 3-butenyl group, a 1-pentenyl group, a 2-pentenyl group, a 3-pentenyl group, a 4-pentenyl group, a 1-cyclopentenyl group, a 3-cyclopentenyl group, a 1-hexenyl group, a 2-hexenyl group, a 3-hexenyl group, a 4-hexenyl group, a 5-hexenyl group, a 4-methyl-3-pentenyl group, a 4,8-dimethyl-3,7-nonadienyl group, a 1-cyclohexenyl group, a 3-cyclohexenyl group, a 1,5-dimethyl-4-hexenyl group, a 1,5-dimethyl-1,4-hexadienyl group, a 1,5,9-trimethyl-4,8-decadienyl group, etc.

The aryl group includes, for example, an aryl group having 6 to 14 carbon atoms. Specifically, examples thereof include a phenyl group, a naphthyl group, an anthryl group, a phenanthryl group, a biphenyl group, etc.

As the aralkyl group, for example, an aralkyl group having 7 to 12 carbon atoms is preferred. Specifically, examples thereof include a benzyl group, a 2-phenylethyl group, a 1-phenylpropyl group, etc.

Each of the groups $R^1$ to $R^3$ other than a hydrogen atom may have a substituent. Examples of the substituent include an alkenyl group, an alkynyl group, an aryl group, an aliphatic heterocyclic group, an aromatic heterocyclic group, an alkoxy group, an alkylenedioxy group, an aryloxy group, an aralkyloxy group, a heteroaryloxy group, an amino group, a substituted amino group, a nitro group, a cyano group, an alkoxycarbonyl group, a halogen atom, an alkyl halide group, etc.

The alkenyl group as the substituent on $R^1$ to $R^3$ may be a straight chain or branched alkenyl group and includes, for example, an alkenyl group having 2 to 20 carbon atoms, preferably 2 to 10 carbon atoms, more preferably 2 to 6 carbon atoms. Specifically, examples thereof include a vinyl group, a propenyl group, a 1-butenyl group, a pentenyl group, a hexenyl group, etc.

The alkynyl group as the substituent on $R^1$ to $R^3$ may be a straight chain or branched alkynyl group and includes, for example, an alkynyl group having 2 to 15 carbon atoms, preferably 2 to 10 carbon atoms, more preferably 2 to 6 carbon atoms. Specifically, examples thereof include an ethynyl group, a 1-propynyl group, a 2-propynyl group, a 1-butynyl group, a 3-butynyl group, a pentynyl group, a hexynyl group, etc.

The aryl group as the substituent on $R^1$ to $R^3$ includes, for example, an aryl group having 6 to 14 carbon atoms. Specifically, examples thereof include a phenyl group, a naphthyl group, an anthryl group, a phenanthryl group, a biphenyl group, a tolyl group, a xylyl group, a mesityl group, a methoxyphenyl group, a dimethoxyphenyl group, a fluorophenyl group, etc.

The aliphatic heterocyclic group as the substituent on $R^1$ to $R^3$ includes, for example, a group having 2 to 14 carbon atoms and containing at least one, preferably 1 to 3, hetero atoms such as nitrogen atom, oxygen atom and sulfur atom. Preferably, the aliphatic heterocyclic group includes a 5- or 6-membered monocyclic aliphatic heterocyclic group and a polycyclic or condensed ring aliphatic heterocyclic group.

Specific examples of the aliphatic heterocyclic group include a 2-oxo-1-pyrrolidinyl group, a piperidino group, a piperazinyl group, a morpholino group, a tetrahydrofuryl group, a tetrahydropyranyl group, a tetrahydrothienyl group, etc.

The aromatic heterocyclic group as the substituent on $R^1$ to $R^3$ includes, for example, a group having 2 to 15 carbon atoms, preferably 3 to 11 carbon atoms, and containing at least one, preferably 1 to 3, hetero atoms such as nitrogen atom, oxygen atom and sulfur atom. Preferably, the aromatic heterocyclic group includes a 5- or 6-membered monocyclic aromatic heterocyclic group and a polycyclic or condensed ring aromatic heterocyclic group.

Specific examples of the aromatic heterocyclic group include a furyl group, a thienyl group, a pyridyl group, a pyrimidinyl group, a pyrazinyl group, a pyridazinyl group, a pyrazolinyl group, an imidazolyl group, an oxazolinyl group, a thiazolinyl group, a benzofuryl group, a benzothienyl group, a quinolyl group, an isoquinolyl group, a quinoxalinyl group, a phtharazinyl group, a quinazolinyl group, a naphthylidinyl group, a cinnolinyl group, a benzimidazolyl group, a benzoxazolyl group, a benzothiazolyl group, etc.

The alkoxy group as the substituent on $R^1$ to $R^3$ includes, for example, a straight chain or branched alkoxy group having 1 to 6 carbon atoms. Specifically, examples thereof include a methoxy group, an ethoxy group, a n-propoxy group, an isopropoxy group, a n-butoxy group, a 2-butoxy group, an isobutoxy group, a tert-butoxy group, a n-pentyloxy group, a 2-methylbutoxy group, a 3-methylbutoxy group, a 2,2-dimethylpropoxy group, a n-hexyloxy group, a 2-methylpentyloxy group, a 3-methylpentyloxy group, a 4-methylpentyloxy group, a 5-methylpentyloxy group, etc.

The alkylenedioxy group as the substituent on $R^1$ to $R^3$ includes, for example, an alkylenedioxy group having 1 to 3 carbon atoms. Specifically, examples thereof include a methylenedioxy group, an ethylenedioxy group, a propylenedioxy group, an isopropylidenedioxy group, etc.

The aryloxy group as the substituent on $R^1$ to $R^3$ includes, for example, an aryloxy group having 6 to 14 carbon atoms. Specifically, examples thereof include a phenoxy group, a naphthyloxy group, an anthryloxy group, etc.

The aralkyloxy group as the substituent group for $R^1$ to $R^3$ includes, for example, an aralkyloxy group having 7 to 12 carbon atoms. Specifically, examples thereof include a benzyloxy group, a 2-phenylethoxy group, a 1-phenylpropoxy group, a 2-phenylpropoxy group, a 3-phenylpropoxy group, a 1-phenylbutoxy group, a 2-phenylbutoxy group, a 3-phenylbutoxy group, a 4-phenylbutoxy group, a 1-phenylpentyloxy group, a 2-phenylpentyloxy group, a 3-phenylpentyloxy group, a 4-phenylpentyloxy group, a 5-phenylpentyloxy group, a 1-phenylhexyloxy group, a 2-phenylhexyloxy group, a 3-phenylhexyloxy group, a 4-phenylhexyloxy group, a 5-phenylhexyloxy group, a 6-phenylhexyloxy group, etc.

The heteroaryloxy group as the substituent on $R^1$ to $R^3$ includes, for example, a heteroaryloxy group having 2 to 14 carbon atoms and containing at least one, preferably 1 to 3, hetero atoms such as nitrogen atom, oxygen atom and sulfur atom. Specifically, examples thereof include a 2-pyridyloxy group, a 2-pyrazyloxy group, a 2-pyrimidyloxy group, a 2-quinolyloxy group, etc.

Examples of the substituted amino group as the substituent on $R^1$ to $R^3$ include a mono- or dialkylamino group, such as N-methylamino group, N,N-dimethylamino group, N,N-diethylamino group, N,N-diisopropylamino group and N-cyclohexylamino group; a mono- or diarylamino group, such as N-phenylamino group, N,N-diphenylamino group, N-naphthylamino group and N-naphthyl-N-phenylamino group; and a mono- or diaralkylamino group, such as N-benzylamino group and N,N-dibenzylamino group; etc.

The alkoxycarbonyl group as the substituent on $R^1$ to $R^3$ is preferably, for example, an alkoxycarbonyl group having 1 to 30 carbon atoms. Specifically, examples thereof include a methoxycarbonyl group, an ethoxycarbonyl group, a n-propoxycarbonyl group, an isopropoxycarbonyl group, a n-butoxycarbonyl group, a 2-butoxycarbonyl group, an isobutoxycarbonyl group, a tert-butoxycarbonyl group, a n-pentyloxycarbonyl group, a 2-methylbutoxycarbonyl group, a 3-methylbutoxycarbonyl group, a 2,2-dimethylpropoxycarbonyl group, a n-hexyloxycarbonyl group, a 2-methylpentyloxycarbonyl group, a 3-methylpentyloxycarbonyl group, a 4-methylpentyloxycarbonyl group, a 5-methylpentyloxycarbonyl group, a cyclopentyloxycarbonyl group, a cyclohexyloxycarbonyl group, a dicyclopentylmethoxycarbonyl group, a dicyclohexylmethoxycarbonyl group, a tricyclopentylmethoxycarbonyl group, a tricyclohexylmethoxycarbonyl group, a phenylmethoxycarbonyl group, a diphenylmethoxycarbonyl group, a triphenylmethoxycarbonyl group, etc.

Examples of the halogen atom as the substituent on $R^1$ to $R^3$ include a fluorine atom, a chlorine atom, a bromine atom, an iodine atom, etc.

The alkyl halide group as the substituent on $R^1$ to $R^3$ is preferably, for example, a perhalogenoalkyl group having 1 to 10 carbon atoms. Specifically, examples thereof include a trifluoromethyl group, a pentafluoroethyl group, a heptafluoropropyl group, an undecafluoropentyl group, a heptadecafluorooctyl group, an undecafluorocyclohexyl group, a dichloromethyl group, etc.

In the compound represented by formula (1), examples of the ring formed by $R^1$ and $R^2$ or $R^1$ and $R^3$ include a cyclopentane ring, a cyclohexane ring, an indane ring, a tetralin ring, a cyclopentene ring, a cyclohexene ring, a cycloheptene ring, an indene ring, a dihydronaphthalene ring, an octahydronaphthalene ring, a decahydronaphthalene ring, etc. These rings may be substituted with the above-described alkyl group or the like.

In the compound represented by formula (2), examples of the ring formed by $R^1$ and $R^2$ or $R^1$ and $R^3$ include a cyclopentane ring, a cyclohexane ring, an indane ring, a tetralin ring, a cyclopentene ring, a cyclohexene ring, a cycloheptene ring, an indene ring, a dihydronaphthalene ring, an octahydronaphthalene ring, a decahydronaphthalene ring, etc. These rings may be substituted with the above-described alkyl group or the like.

Among those described above, each of $R^1$, $R^2$ and $R^3$ is preferably a hydrogen atom, an alkyl group having 1 to 13 carbon atoms, which may have a substituent group, or an alkenyl group having 2 to 13 carbon atoms, which may have a substituent.

The alkyl group having 1 to 13 carbon atoms, which may have a substituent, is preferably, for example, a straight chain or branched alkyl group having 1 to 13 carbon atoms. Specifically, examples thereof include a methyl group, an ethyl group, a n-propyl group, an isopropyl group, a n-butyl group, a 2-butyl group, an isobutyl group, a tert-butyl group, a n-pentyl group, a 2-pentyl group, a 3-pentyl group, a tert-pentyl group, a 2-methylbutyl group, a 3-methylbutyl group, a 2,2-dimethylpropyl group, a 1,2-dimethylpropyl group, a n-hexyl group, a 2-hexyl group, a 3-hexyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 2-ethylbutyl group, a 1,3,3-trimethylbutyl group, a 1,1,2-trimethylpropyl group, a 1,2,2-trimethylpropyl group, a 1-ethyl-1-methylpropyl group, a 1-ethyl-2-methylpropyl group, a heptyl group, an octyl group, a 1,5-dimethylhexyl group, a nonyl group, a decyl group, an undecyl group, a dodecyl group, a tridecyl group, a 1,5,9-trimethyldecyl group, a 4-methylpentyl group, a 1,5-dimethylhexyl group, etc.

As the alkenyl group having 2 to 13 carbon atoms, which may have a substituent, for example, a straight chain or branched alkenyl group having 2 to 13 carbon atoms, and a cyclic alkenyl group having 3 to 13 carbon atoms, are preferred. Specifically, examples thereof include a vinyl group, a 1-propenyl group, a 2-propenyl group, a 1-butenyl group, a 2-butenyl group, a 3-butenyl group, a 1-pentenyl group, a 2-pentenyl group, a 3-pentenyl group, a 4-pentenyl group, a 1-cyclopentenyl group, a 3-cyclopentenyl group, a 1-hexenyl group, a 2-hexenyl group, a 3-hexenyl group, a 4-hexenyl group, a 5-hexenyl group, a 4-methyl-3-pentenyl group, a 1-octenyl group, a 2-octenyl group, a 4,8-dimethyl-3,7-nonadienyl group, a 1-cyclohexenyl group, a 3-cyclohexenyl group, a 4-methyl-3-pentenyl group, a 1,5-dimethyl-1,4-hexadienyl group, a 1,5-dimethyl-4-hexenyl group, a 1,5,9-trimethyl-4,8-decadienyl group, etc.

As for more preferred examples of $R^1$, $R^2$ and $R^3$, in view of flavor or fragrance and deodorizing effect, each of $R^1$ and $R^2$ is an alkyl group having 1 to 8 carbon atoms, an alkenyl group having 2 to 8 carbon atoms, or a hydrogen atom, and $R^3$ is a hydrogen atom.

The alkyl group having 1 to 8 carbon atoms is preferably, for example, a straight chain or branched alkyl group having 1 to 8 carbon atoms. Specifically, examples thereof include a methyl group, an ethyl group, a n-propyl group, an isopropyl group, a n-butyl group, a 2-butyl group, an isobutyl group, a tert-butyl group, a n-pentyl group, a 2-pentyl group, a 3-pentyl group, a tert-pentyl group, a 2-methylbutyl group, a 3-methylbutyl group, a 2,2-dimethylpropyl group, a 1,2-dimethylpropyl group, a n-hexyl group, a 2-hexyl group, a 3-hexyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 2-ethylbutyl group, a 1,3,3-trimethylbutyl group, a 1,1,2-trimethylpropyl group, a 1,2,2-trimethylpropyl group, a 1-ethyl-1-methylpropyl group, a 1-ethyl-2-methylpropyl group, a heptyl group, an octyl group, a 1,5-dimethylhexyl group, a 4-methylpentyl group, a 1,5-dimethylhexyl group, etc.

As the alkenyl group having 2 to 8 carbon atoms, specifically, examples thereof include a vinyl group, a 1-propenyl group, a 2-propenyl group, a 1-butenyl group, a 2-butenyl group, a 3-butenyl group, a 1-pentenyl group, a 2-pentenyl group, a 3-pentenyl group, a 4-pentenyl group, a 1-cyclopentenyl group, a 3-cyclopentenyl group, a 1-hexenyl group, a 2-hexenyl group, a 3-hexenyl group, a 4-hexenyl group, a 5-hexenyl group, a 4-methyl-3-pentenyl group, a 1-octenyl group, a 2-octenyl group, a 1-cyclohexenyl group, a 3-cyclohexenyl group, a 4-methyl-3-pentenyl group, a 1,5-dimethyl-1,4-hexadienyl group, a 1,5-dimethyl-4-hexenyl group, etc.

In the case of forming a ring by $R^1$ and $R^2$ or $R^1$ and $R^3$, in view of flavor or fragrance and deodorizing effect, a cyclohexene ring and a cyclohexane group are preferred.

The substituent substituted on the cyclohexene ring and cyclohexane ring is preferably an alkyl group having 1 to 3 carbon atoms. The substitution may be a single substitution or a plurality of substitutions.

The alkyl group having 1 to 3 carbon atoms is preferably, for example, a straight chain or branched alkyl group having 1 to 3 carbon atoms. Specifically, examples thereof include a methyl group, an ethyl group, an n-propyl group, an isopropyl group, etc.

(Group Represented by Ar)

The aryl group represented by Ar, which may have a substituent, is described.

The aryl group includes, for example, an aryl group having 6 to 14 carbon atoms. Specifically, examples thereof include a phenyl group, a naphthyl group, an anthryl group, a biphenyl group, etc.

Among these, in view of fragrance emission performance and deodorizing effect, a phenyl group is preferred.

The substituent which may be substituted on the aryl group includes, for example, an alkyl group having 1 to 8 carbon atoms. Specifically, examples thereof include a methyl group, an ethyl group, a n-propyl group, an isopropyl group, a n-butyl group, a 2-butyl group, an isobutyl group, a tert-butyl group, a n-pentyl group, a 2-pentyl group, a 3-pentyl group, a tert-pentyl group, a 2-methylbutyl group, a 3-methylbutyl group, a 2,2-dimethylpropyl group, a 1,2-dimethylpropyl group, a n-hexyl group, a 2-hexyl group, a 3-hexyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 2-ethylbutyl group, a 1,3,3-trimethylbutyl group, a 1,1,2-trimethylpropyl group, a 1,2,2-trimethylpropyl group, a 1-ethyl-1-methylpropyl group, a 1-ethyl-2-methylpropyl group, a heptyl group, an octyl group, a 1,5-dimethylhexyl group, a 4-methylpentyl group, a 1,5-dimethylhexyl group, etc. Among these, a methyl group is preferred.

(Specific Examples of Compound Represented by Formula (1))

Specific examples of the compound represented by formula (1) of the present invention include the compounds shown below. In the compounds illustrated below, the wavy line indicates either one of E and Z geometric isomers or a mixture thereof

[Chem. 15]

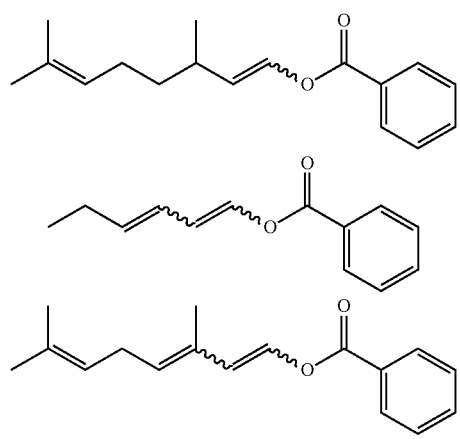

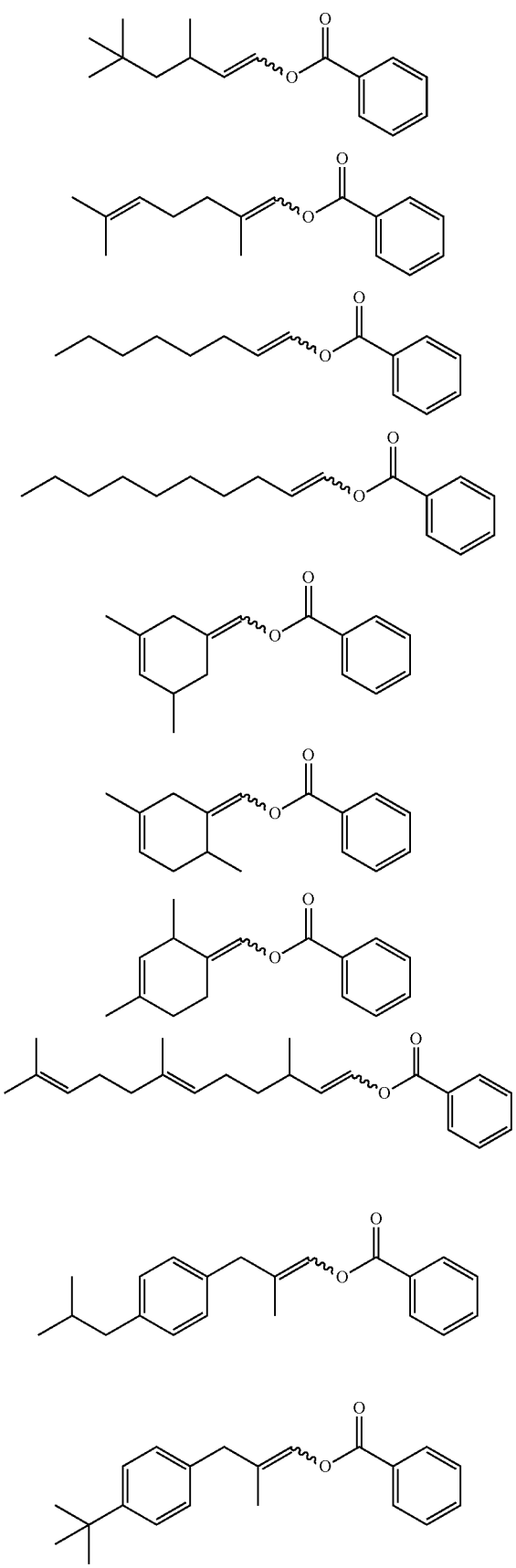

-continued

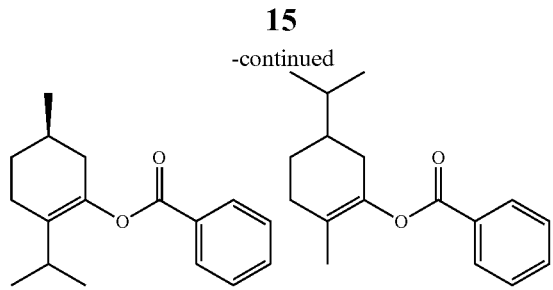

As for the compound represented by formula (1) of the present invention, particularly, in view of fragrance, fragrance emission performance and deodorizing effect, a compound represented by the following formula (3) and a compound represented by formula (4) are preferred.

[Chem. 16]

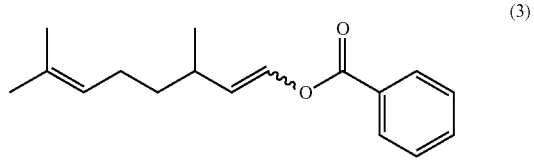
(3)

In formula (3), the wavy line indicates either one of E and Z geometric isomers or a mixture thereof.

[Chem. 17]

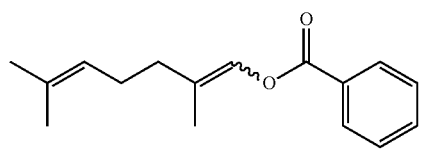
(4)

In formula (4), the wavy line indicates either one of E and Z geometric isomers or a mixture thereof (Synthesis Method of Compound Represented by Formula (1))

The compound represented by formula (1) used in the present invention can be easily synthesized by a known method.

Out of the compounds represented by formula (1), a production method of 3,7-dimethylocta-1,6-dienyl benzoate represented by the following formula (3) is described.

The compound represented by formula (3) can be synthesized according to the method described, for example, in Helv. Chim. Acta. 1988, 71, 1000-1004. This method can be represented by Scheme 1 below.

Scheme 1

[Chem. 18]

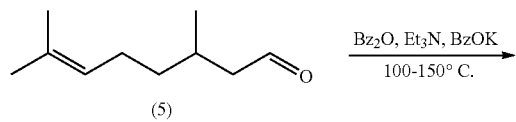

-continued

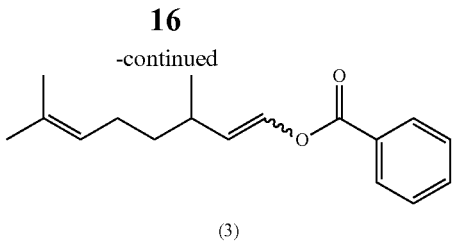
(3)

As for the synthesis of the compound represented by formula (3), the compound can be prepared by reacting a mixed solution of citronellal (compound of formula (5)), benzoic anhydride, triethylamine, and benzoate salt at a temperature ranging from 100 to 150° C. As the used benzoate salt, potassium benzoate and sodium benzoate are preferred.

The thus-obtained compound of formula (3) can be isolated in the usual manner, such as extraction, distillation, recrystallization or chromatography of every sort.

In the compound of formula (3), the wavy line represents either one of E and Z geometric isomers or a mixture thereof (Flavor or Fragrance Component)

The compound represented by formula (1) of the present invention can be used as a flavor or fragrance precursor. By allowing a hydrolysate to act on the compound represented by formula (1), an aldehyde or ketone represented by formula (2), which is a flavor or fragrance component, can be released.

The hydrolysate includes lipase, protease, amylase, glycosidase, etc., and among these, in view of hydrolysis rate, lipase is preferred.

The lipase is not particularly limited and, as long as it is an enzyme that breaks down fat, may be a naturally occurring material or a formulated commercial product.

The aldehyde represented by formula (2), which is a flavor or fragrance component or the later-described deodorizing component, includes a straight chain or branched aliphatic aldehyde having 6 to 13 carbon atoms, trans-2-hexenal, cis-3-hexenal, 2,6-nonadienal, cis-4-decenal, trans-4-decenal, undecylene aldehyde, trans-2-dodecenal, trimethylundecenal, 2,6,10-trimethyl-5,9-undecadienal, 2,6-dimethyl-5-heptenal, citral, citronellal, hydroxycitronellal, perillaldehyde, citronellyloxyacetaldehyde, 2,4-dimethyl-3-cyclohexenylcarboxyaldehyde, 2,4,6-trimethyl-3-cyclohexene-1-carboxyaldehyde, 5-methoxy-octahydro-4,7-methano-1H-indene-2-carboxyaldehyde, 4-(4-methyl-3-pentenyl)-3-cyclohexene-1-carboxyaldehyde, 4-(4-hydroxy-4-methyl-pentyl)-3-cyclohexene-1-carboxyaldehyde, 1-methyl-4-(4-methyl-pentyl)-3-cyclohexene-carboxyaldehyde, 4-(tricyclo[5.2.1.0$^{2,6}$]decylidene-8)-butenal, 2-methyl-4-(2,6,6-trimethyl-2-cyclohexene-1-yl)-butanal, benzaldehyde, phenylacetoaldehyde, phenylpropylaldehyde, cinnamic aldehyde, α-amylcinnamic aldehyde, α-hexylcinnamic aldehyde, 2-phenylpropanal, anisaldehyde, p-methylphenylacetoaldehyde, cuminaldehyde, cyclamen aldehyde, 3-(p-tert-butylphenyl)-propylaldehyde, p-ethyl-2,2-dimethylhydrocinnamaldehyde, 2-methyl-3-(p-methoxyphenyl)-propylaldehyde, 4-tert-butyl-α-methylhydrocinnamic aldehyde, salicylaldehyde, heliotropin, 2-methyl-3-(3,4-methylenedioxy-phenyl)-propanal, vanillin, ethylvanillin, methylvanillin, farnesal, dihydrofamesal, 3,5,5-trimethylhexanal, octanal, etc.

The ketone represented by formula (2), which is a flavor or fragrance component or the later-described deodorizing component, includes methyl amyl ketone, ethyl amyl ketone, methyl hexyl ketone, methyl nonyl ketone, methylheptenone, Koavone, camphor, carvone, menthone, isomenthone, pulegone, piperitone, fenchone, geranylacetone, cedryl methyl ketone, nootkatone, α-ionone, β-ionone, α-methylionone, β-methylionone, α-isomethylionone, β-isomethylionone, allylionone, α-irone, β-irone, γ-irone, α-damascone, β-damascone, δ-damascone, damascenone, α-dinascone, β-dinascone, maltol, ethylmaltol, 2,5-dimethyl-4-hydroxyfuranone, 4,5-dimethyl-3-hydroxy-5H-furan-2-one, p-tert-butylcyclohexanone, amylcyclopentanone, heptylcyclopentanone, dihydrojasmone, cis-jasmone, 7-methyl-octahydro-1,4-methanonaphthlen-6(2H)-one, 4-cyclohexyl-4-methyl-2-pentanone, 2,2,5-trimethyl-5-pentylcyclopentanone, 4-(1-ethoxyvinyl)-3,3,5,5-tetramethylcyclohexanone, 6,7-dihydro-1,1,2,3,3-pentamethyl-4(5H)-indanone, 7-acetyl-1,2,3,4,5,6,7,8-octahydro-1,1,6,7-tetramethylnaphthalene, acetophenone, p-methylacetophenone, benzyl acetone, 7-methyl-3,4-dihydro-(2H)-1,5-benzodioxepin-3-one, raspberry ketone, anisylacetone, 4-(4-hydroxy-3-methoxyphenyl)-2-butanone, methyl naphthyl ketone, 4-phenyl-4-methyl-2-pentanone, benzophenone, etc.

(Deodorizing Component)

By allowing a microorganism to act on the compound represented by formula (1), an aldehyde or ketone represented by formula (2), which is a deodorizing component, can be released.

The microorganism that can cause the compound represented by formula (1) of the present invention to release, as a deodorizing component, an aldehyde or ketone represented by formula (2) includes *Staphylococcus* bacteria, *Corynebacterium* bacteria, *Propionibacterium* bacteria, *Pseudomonas* bacteria, *Bacillus* bacteria, *Moraxella* bacteria, *Malassezia* fungi, etc.

Specifically, examples thereof include *Staphylococcus aureus*, *Staphylococcus epidermidis*, *Corynebacterium xerosis*, *Propionibacterium acnes*, *Pseudomonas aeruginosa*, *Bacillus subtilis*, *Moraxella osloensis*, *Malassezia furfur*, etc.

[Flavor or Fragrance Composition]

The compound represented by formula (1) of the present invention can be blended in a flavor or fragrance composition. The compound represented by formula (1) can be used singly or in combination of two or more kinds and can also be appropriately used in combination with a known flavor or fragrance component.

Examples of the known flavor or fragrance component include natural essential oils, such as lemon oil, orange oil, lime oil, bergamot oil, lavandin oil, lavender oil, geranium oil, rose oil and sandalwood oil; hydrocarbons, such as α-pinene, β-pinene, limonene, p-cymene and thujone; aliphatic alcohols, such as octanol and p-tert-butylcyclohexanol; terpene-based alcohols, such as menthol, citronellol and geraniol; aromatic alcohols, such as benzyl alcohol and phenylethyl alcohol; aliphatic aldehydes; terpene-based aldehydes; aromatic aldehydes; acetals; chain ketones; cyclic ketones, such as damascone, β-ionone and methylionone; terpene-based ketones, such as carvone, menthone, isomenthone and camphor; aromatic ketones, such as acetophenone and raspberry ketone; ethers, such as dibenzyl ether; oxides, such as linalool oxide and rose oxide; musks, such as cyclopentadecanolide and cyclohexadecanolide; lactones, such as γ-nonalactone, γ-undecalactone and coumarin; aliphatic esters, such as acetic acid ester and propionic acid ester; aromatic esters, such as benzoic acid ester and phenylacetic acid ester; etc.

In the flavor or fragrance composition of the present invention, a solvent, for example, ethanol, isopropyl alcohol, ethylene glycol, propylene glycol, dipropylene glycol, butylene glycol, pentylene glycol, hexylene glycol, polyethylene glycol, diethyl phthalate, isopropyl myristate, triethyl citrate, benzyl benzoate, glycerin, triacetin, benzyl alcohol, paraffin, isoparaffin, a rosin ester derivative such as Hercolyn, etc., glycol ethers such as 3-methoxy-3-methyl-1-butanol, ethyl carbitol (diethylene glycol monoethyl ether), ethylene glycol monomethyl ether, propylene glycol monomethyl ether, ethylene glycol monoethyl ether, dipropylene glycol monomethyl ether, tripropylene glycol methyl ether, dipropylene glycol dimethyl ether, dipropylene glycol propyl ether, dipropylene glycol methyl ether acetate, dipropylene glycol butyl ether, etc., a terpene resin such as pinene polymer, etc., silicones such as cyclic silicone, etc., water, etc., or a fixative may be used.

In addition, a known component, such as higher alcohol, surfactant, antioxidant, ultraviolet absorber, chelating agent, solubilizing agent, stabilizing agent, cooling sensation agent, preservative, antimicrobial, bactericide, fungicide, insecticidal component and coloring matter, may be further mixed, if desired.

The blending amount of the compound represented by formula (1) of the present invention in the flavor or fragrance composition is not strictly restricted and can be variously changed according to use of the flavor or fragrance composition. The blending amount of the compound represented by formula (1) of the present invention in the flavor or fragrance composition is preferably from 0.1 to 95.0% by mass, more preferably from 0.5 to 80.0% by mass.

[Aroma Product, Laundry Care Product, Hair Care Product, Cosmetic, or Cleaner]

The compound represented by formula (1) of the present invention can be used, individually or in combination of two or more kinds, for a product, such as aroma product, laundry care product, hair care product, cosmetic or cleaner.

Furthermore, in the product, such as aroma product, laundry care product, hair care product, cosmetic or cleaner, for the purpose of letting the fragrance emitted from the product itself, the fragrance during use of the product, and the lingering fragrance from clothing, hair or skin be more favorable, in addition to the compound represented by formula (1) of the present invention, there may be appropriately blended in combination a compounded flavor or fragrance; a powder flavor or fragrance of a known core-shell type, a matrix type using starch or processed starch, etc. or a fragrance capsule; a fragrance impregnated body prepared by impregnating an inorganic porous material such as silica gel or calcium silicate or an organic porous material such as celluloses, with a flavor or fragrance; a fragrance inclusion body prepared by the inclusion of a flavor or fragrance in α-cyclodextrin, β-cyclodextrin, γ-cyclodextrin, hydroxypropylated β-dextrin, highly branched cyclic dextrin, etc.; a known flavor or fragrance precursor, pro-fragrance, fragrance precursor, pro-perfume, etc., such as silicic acid ester compound, fatty acid ester compound, acetal compound, hemiacetal compound, Schiff base compound, hemiaminal compound or hydrazone compound, each of which can release a flavor or fragrance component.

Examples of the aroma product include a perfume, eau de cologne, a liquid air freshener, a gel air freshener, a powder air freshener, an impregnated air freshener, a mist spray air freshener, an aerosol spray air freshener, a plug-in air freshener, an incense stick, a candle, etc.

Examples of the laundry care product include a mist spray for clothing, a spray for clothing, a detergent, a fabric softener, etc.

Examples of the hair care product include a hair shampoo, a hair rinse, a hair conditioner, a hair treatment, a hair tonic, a hair styling agent, a hair dye, a permanent waving agent, a hair growth agent, a hair cologne, etc.

Examples of the cosmetic include a lotion, a milky lotion, a cosmetic cream, a soap, a liquid soap, a facial cleanser, a sunscreen, an antiperspirant, a bath additive, a lipstick, a foundation, etc.

Examples of the cleaner include a toilet cleaner, a toilet bowl cleaner, a glass cleaner, a dishwashing detergent, a washing machine cleaner, a drain cleaner, a bathroom cleaner, etc.

The compound represented by formula (1) of the present invention releases a flavor or fragrance component by the action of a hydrolase and therefore, is particularly useful when a product having blended therein the compound represented by formula (1) of the present invention is used in combination with a product having blended therein a hydrolysate.

The method for using the products in combination is not particularly limited but includes a method of using a mutual combination of laundry care products, hair care products, or cosmetics.

As for the mutual combination of laundry care products, examples of the method include (A) a method of using a combination of a cleaner for clothing, in which a lipase is blended, and a mist spray for clothing, a spray for clothing, a fabric softener, etc., in which the compound represented by formula (1) of the present invention is blended, and (B) a method of using a combination of a cleaner for clothing, in which the compound represented by formula (1) of the present invention is blended, and a mist spray for clothing, a spray for clothing, a fabric softener, etc., in which a lipase is blended.

As for the mutual combination of hair care products, examples of the method include (A) a method of using a combination of a shampoo in which a lipase is blended, and a hair rinse, a hair conditioner, a hair treatment, a hair styling agent, a hair growth agent, a hair cologne, etc., in which the compound represented by formula (1) of the present invention is blended, and (B) a method of using a combination of a shampoo in which the compound represented by formula (1) of the present invention is blended, and a hair rinse, a hair conditioner, a hair treatment, a hair styling agent, a hair growth agent, a hair cologne, etc., in which a lipase is blended.

The blending amount of the compound represented by formula (1) of the present invention in each product is not strictly restricted and can be variously changed according to use thereof. The blending amount of the compound represented by formula (1) of the present invention in each product is preferably from 0.0001 to 10% by mass, more preferably from 0.001 to 5% by mass.

[Deodorant]

The compound represented by formula (1) of the present invention can be used, singly or in combination of two or more kinds, for a deodorant.

The deodorant of the present invention can be used after optionally blending one kind or two or more kinds of known components selected from a cleaner, an antimicrobial, a fungicide, a deodorant, a natural essential oil, a flavor or fragrance, an aroma material, a cooling sensation agent, a warming sensation agent, a rust inhibitor, an antifoaming agent, a pH adjusting agent, water, a solvent, a propellant, a surfactant, an insecticide, a repellent, an insect repellent, a water repellent, a degrading enzyme, an antistatic agent, a coloring matter, an ultraviolet absorber, a preservative, a chelating agent, an antioxidant, a thickener, a gellant, a water-absorbing resin, activated carbon, silica, a porous material, a resin, paper, felt, a higher alcohol, an inorganic salt, etc., and formulating the blend.

Examples of the known component include a cleaner such as alkylamine oxide, alkylamine, alkyl polyglycoside, naphthalenesulfonic acid-formalin condensate, hydrolyzed collagen peptide salt, acylmethyltaurine salt, N-acylamino acid salt, alkyl sulfate, ether carboxylate, ether sulfonate, alkyltrimethylammonium chloride, dialkyltrimethylammonium chloride, alkylamine salt, alkyl amidopropyl amino oxide, alkyl betaine, acetic acid betaine, fatty acid soap, etc.; an antimicrobial or fungicide such as 4-chloro-3,5-xylenol, isopropylmethylphenol, thymol, hinokitiol, phenol-based compound, polyphenol, catechin, tannin, natural product containing these, natural product containing their derivative, etc., 2-(4'-thiazolyl)-benzimidazole, benzalkonium chloride, benzethonium chloride, cetylpyridinium chloride, triclosan, silver ion, stabilized chlorine dioxide, etc.; a deodorant such as lauryl methacrylate, methacrylate, geranyl crotonate, myristic acid acetophenone, glyoxal, abietic acid, flavonoid, polyphenol, plant extract, amphoteric surfactant, zinc ricinoleate, etc.; a natural essential oil such as lemon oil, orange oil, lime oil, bergamot oil, lavandin oil, lavender oil, geranium oil, rose oil, sandalwood oil, etc.; a flavor or fragrance, for example, hydrocarbons such as $\alpha$-pinene, $\beta$-pinene, limonene, p-cymene, thujone, etc., aliphatic alcohols such as octanol, p-tert-butylcyclohexanol, etc., terpene-based alcohols such as menthol, citronellol, geraniol, etc., aromatic alcohols such as benzyl alcohol, phenylethyl alcohol, etc., aliphatic aldehydes, terpene-based aldehydes, aromatic aldehydes, acetals, chain ketones, cyclic ketones such as damascone, $\beta$-ionone, methylionone, etc., terpene-based ketones such as carvone, menthone, isomenthone, camphor, etc., aromatic ketones such as acetophenone, raspberry ketone, etc., ethers such as dibenzyl ether, etc., oxides such as linalool oxide, rose oxide, etc., musks such as cyclopentadecanolide, cyclohexadecanolide, etc., lactones such as $\gamma$-nonalactone, $\gamma$-undecalactone, coumarin, etc., aliphatic esters such as acetic acid ester, propionic acid ester, etc., and aromatic esters such as benzoic acid ester, phenylacetic acid ester, etc.; a compounded flavor or fragrance prepared from the above-described natural essential oil and flavor or fragrance; a powder flavor or fragrance of a known core-shell type, a matrix type using starch or processed starch, etc. or a fragrance capsule; a fragrance impregnated body prepared by impregnating an inorganic porous material such as silica gel, calcium silicate, etc., or an organic porous material such as celluloses, etc., with a flavor or fragrance; a fragrance inclusion body prepared by the inclusion of a flavor or fragrance in $\alpha$-cyclodextrin, $\beta$-cyclodextrin, $\gamma$-cyclodextrin, hydroxypropylated $\beta$-dextrin, highly branched cyclic dextrin, etc.; a known aroma material, for example, flavor or fragrance precursor, pro-fragrance, fragrance precursor, pro-perfume, etc., such as silicic acid ester compound, fatty acid ester compound, acetal compound, hemiacetal compound, Schiff base compound, hemiaminal compound, hydrazone compound, etc., which can release a flavor or fragrance component; a rust inhibitor such as trisodium citrate, ammonium citrate, sodium nitrite, ammonium benzoate, ammonium nitride, etc.; an antifoaming agent such as silicone, etc.; a pH adjusting agent such as citric acid, sodium monohydrogenphosphate, sodium dihydrogenphosphate, potassium monohydrogenphosphate, potassium dihydrogenphosphate, etc.; a solvent, for example, water, ethyl alcohol, propyl alcohol, isopropyl alcohol, butyl alcohol, modified alcohol, ethylene glycol, propylene glycol, dipropylene glycol, butylene glycol, pentylene glycol, hexylene glycol, polyethylene glycol, diethyl phthalate, isopropyl myristate, triethyl citrate, benzyl benzoate, glycerin, triacetin, benzyl alcohol, paraffin, isoparaffin, a rosin ester such as Hercolyn, etc., glycol ethers such as 3-methoxy-3-methyl-1-butanol, ethyl carbitol (diethylene glycol monoethyl ether), ethylene glycol monomethyl ether, propylene glycol monomethyl ether, ethylene glycol monoethyl ether, dipropylene glycol monomethyl ether, tripropylene glycol methyl ether, dipropylene glycol dimethyl ether, dipropylene glycol propyl ether, dipropylene glycol methyl ether acetate, dipropylene glycol butyl ether, etc., a terpene resin such as pinene polymer, etc., and silicones such as cyclic silicone, etc.; a propellant, for example, a liquefied petroleum gas such as propane, n-butane, isobutane, etc. a liquefied gas such as dimethyl ether, CFC (Chloro Fluoro Carbon), HCFC (Hydro Chloro Fluoro Carbon), HFC (Hydro Fluoro Carbon), etc., and a compressed gas such as nitrogen, carbon dioxide, compressed air, nitrous oxide, etc.; and a surfactant such as polyoxyethylene alkyl ether, polyoxyethylene polyoxypropylene copolymer, hydrogenated caster oil, sorbitan fatty acid ester, etc.

Examples of the formulated deodorant of the present invention includes a deodorizing mist, a deodorizing spray, a liquid deodorant, a gel deodorant, a solid deodorant, a sheet-shaped deodorant, a granular deodorant, a beads deodorant, a powder deodorant, a smoke deodorant, a deodorant for toilet odor, a deodorant for urine odor, a deodorant for body odor, a deodorant for sweat odor, a deodorant for foot odor, a deodorant for scalp odor, a deodorant for aging odor, a deodorant for nursing care, a deodorant for raw garbage odor, a fabric deodorizer, a deodorant for damp-dry odor, a deodorant for laundry care, a deodorant for shoe cupboards, a shoe deodorizer, an entrance deodorizer, a room deodorizer, a bedroom deodorizer, a car freshener, a deodorant for drain odor, a deodorant for pets, a deodorant for diapers, a deodorant for closets, a deodorant for air conditioners, etc.

The deodorant of the present invention can be used in a product such as aroma product, laundry care product, hair care product, cosmetic, oral care product, hygiene product, insecticide, insect repellent, dehumidifying agent, cleaner, etc.

Examples of the aroma product include a liquid air freshener, a gel air freshener, a powder air freshener, an impregnated air freshener, a beads air freshener, a paper air freshener, a permeable film air fresher, a plug-type air freshener, a fan-type air freshener, an ultrasonic air freshener, a water-absorbing polymer air freshener, a mist spray air freshener, an aerosol spray air freshener, a plug-in air freshener, an incense stick, a candle, a reed diffuser, etc., in which a deodorizing function is imparted.

Examples of the laundry care product include a mist spray for clothing, a spray for clothing, a detergent, a fabric softener, an anti-wrinkle agent, etc., in which a deodorizing function is imparted.

Examples of the hair care product include a hair shampoo, a hair rinse, a hair conditioner, a hair treatment, a hair tonic, a hair styling agent, a hair dye, a permanent waving agent, a hair growth agent, a hair lotion, a hair spray, etc., in which a deodorizing function is imparted.

Examples of the cosmetic include a lotion, a milky lotion, a cosmetic cream, a soap, a liquid soap, a facial cleanser, a sunscreen, an antiperspirant, a bath additive, a lipstick, a foundation, etc., in which a deodorizing function is imparted.

Examples of the oral care product include a toothpaste, a mouthwash, a mouth spray, a mouth freshener, a denture care product, a breath freshening product, etc., in which a deodorizing function is imparted.

Examples of the hygiene product include a paper diaper, a sanitary product, wet tissue, tissue paper, toilet paper, a mask, etc., in which a deodorizing function is imparted.

Examples of the cleaner include a toilet cleaner, a toilet bowl cleaner, a glass cleaner, a dishwashing detergent, a washing machine cleaner, a drain cleaner, a bathroom cleaner, a denture etc., in which a deodorizing function is imparted.

The blending amount of the compound represented by formula (1) of the present invention in each product is not strictly restricted and can be variously changed according to use thereof. The blending amount of the compound represented by formula (1) of the present invention in each product is preferably from 0.0001 to 10% by mass, more preferably from 0.001 to 5% by mass.

EXAMPLES

The present invention is hereunder specifically described by reference to Examples, but it should be understood that the present invention is by no means limited by these Examples.

Test Example 1

(Example 1-1) Synthesis of 2-isopropyl-5-methyl-1-cyclohexenyl Benzoate

[Chem. 19]

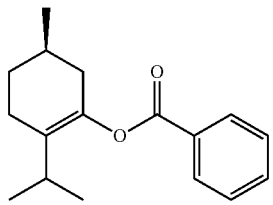

To a mixed solution of (−)-menthone 4.63 g (30 mmol) and benzoic anhydride 2.26 g (10 mmol), p-toluenesulfonic acid monohydrate 95 mg (0.5 mmol) was added at room temperature, followed by stirring at 100 to 110° C. (internal temperature) for 4.5 hours.

After cooling the reaction solution, the reaction was quenched by adding toluene and water. The reaction solution was extracted with toluene, and the organic layer was washed with a saturated sodium hydrogencarbonate aqueous solution and water. After drying the organic layer over sodium sulfate, the filtrate was concentrated under reduced pressure to obtain a crude product. The resulting crude product was purified by silica gel column chromatography to obtain 1.90 g of the target product.

(Example 1-2) Synthesis of 1,3-hexadienyl Benzoate

[Chem. 20]

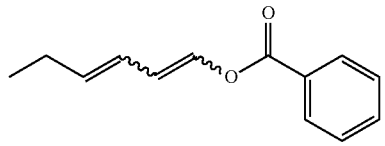

To a mixed solution of 2-hexenal 7.85 g (80 mmol), triethylamine 14.5 ml (104 mmol) and sodium benzoate 692 mg (4.8 mmol), benzoic anhydride 29.0 g (128 mmol) was added at room temperature, followed by stirring at 115 to 120° C. (internal temperature) for 8 hours.

After cooling the reaction solution, the reaction was quenched by adding toluene and water. The reaction solution was extracted with toluene, and the organic layer was washed with a saturated sodium hydrogencarbonate aqueous solution and water. After drying the organic layer over sodium sulfate, the filtrate was concentrated under reduced pressure to obtain a crude product. The resulting crude product was purified by silica gel column chromatography to obtain 13.26 g of the target product.

(Example 1-3) Synthesis of 3,7-dimethylocta-1,3,6-trienyl Benzoate

[Chem. 21]

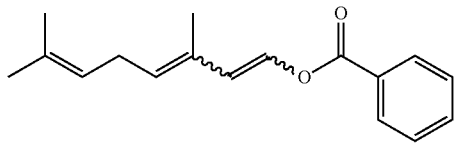

To a mixed solution of citral 1.52 g (10 mmol) and pyridine 3.15 ml (39 mmol), benzoic anhydride 4.52 g (39 mmol) was added at room temperature, followed by stirring at 132 to 138° C. (internal temperature) for 7.5 hours.

After cooling the reaction solution, the reaction was quenched by adding toluene and water. The reaction solution was extracted with toluene, and the organic layer was washed with 1 N hydrochloric acid, a saturated sodium hydrogencarbonate aqueous solution and saturated brine. After drying the organic layer over sodium sulfate, the filtrate was concentrated under reduced pressure to obtain a crude product. The resulting crude product was purified by silica gel column chromatography to obtain 1.60 g of the target product.

(Example 1-4) Synthesis of 3,7-dimethylocta-1,6-dienyl Benzoate

[Chem. 22]

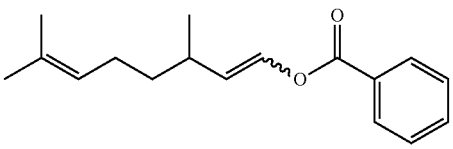

To a mixed solution of 1-citronellal 9.62 g (60 mmol), triethylamine 10.9 ml (78 mmol) and sodium benzoate 519 mg (3.6 mmol), benzoic anhydride 21.7 g (96 mmol) was added at room temperature, followed by stirring at 112 to 118° C. (internal temperature) for 10 hours.

After cooling the reaction solution, the reaction was quenched by adding toluene and water. The reaction solution was extracted with toluene, and the organic layer was washed with a saturated sodium hydrogencarbonate aqueous solution and water. After drying the organic layer over sodium sulfate, the filtrate was concentrated under reduced pressure to obtain a crude product. The resulting crude product was purified by silica gel column chromatography to obtain 9.38 g of the target product.

(Example 1-5) Synthesis of 2,6-dimethylhepta-1,5-dienyl Benzoate

[Chem. 23]

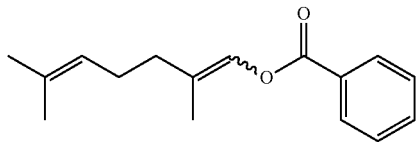

To a mixed solution of 2,6-dimethyl-5-heptenal 1.40 g (10 mmol), triethylamine 1.81 ml (13 mmol) and sodium benzoate 86 mg (0.6 mmol), benzoic anhydride 3.62 g (16 mmol) was added at room temperature, followed by stirring at 110 to 120° C. (internal temperature) for 10.5 hours.

After cooling the reaction solution, the reaction was quenched by adding toluene and water. The reaction solution was extracted with toluene, and the organic layer was washed with a saturated sodium hydrogencarbonate aqueous solution and water. After drying the organic layer over sodium sulfate, the filtrate was concentrated under reduced pressure to obtain a crude product. The resulting crude product was purified by silica gel column chromatography to obtain 1.85 g of the target product.

Examples 1-6 to 1-9

LIPASE-Induced Fragrance Emission Test:

10 mg of each of the compounds of Examples 1-1 to 1-3 and 1 g of an aqueous 1% lipase preparation solution were charged in a vial bottle and mixed and after hermetically sealing the bottle, the mixture was subjected to GC/MS analysis of the head space component to obtain a peak area of the fragrance emitting compound. As a control, water was used in place of the aqueous 1% lipase preparation solution, and the peak area of the control was obtained by the same method.

The fragrance emission amount was determined from the difference between the peak area of the obtained fragrance emitting compound and the peak area of the control. The results are shown in Table 1. As the lipase preparation, Lipex 100 L produced by Novozymes, and AY "Amano" 30SD produced by Amano Enzyme Inc. were used.

(GC/MS Measurement Conditions)
 Measuring apparatus: 7890GC/5975MSD (manufactured by Agilent Technologies)
 Column: BC-WAX 50 m×0.25 mm I.D.
 Temperature rise: 70° C.→220° C., 4° C./min
 Split ratio: 60:1

TABLE 1

| Compound | Example 1-6 Compound of Example 1-1 | Example 1-7 Compound of Example 1-2 | Example 1-8 Compound of Example 1-3 | Example 1-9 Compound of Example 1-3 |
|---|---|---|---|---|
| Fragrance emission amount | 76,407,359 | 12,076,381 | 5,098,870 | 16,031,669 |
| Fragrance emitting compound | menthone | hexenal | citral | citral |
| Lipase preparation | | Lipex 100L | | AY "Amano" 30SD |

It was confirmed from the results of Table 1 that the compound represented by formula (1) according to the present invention releases an aromatic aldehyde or an aromatic ketone by the action of lipase and has an effect as a flavor or fragrance precursor.

Examples 1-10 and 1-11

Test for Confirming Fragrance Emission from Hair at the Time of Use of Shampoo:

A shampoo was prepared according to a formulation shown in Table 2. A hair bundle of 10 cm in length was cleaned using the prepared shampoo and rinsed with tap water. After drying at room temperature for 15 hours, about 0.3 g of an aqueous 1% lipase preparation solution was sprayed onto the hair bundle, and the scent on the hair bundle was smelled to examine the presence or absence of fragrance emission from hair. As the lipase preparation, AY "Amano" 30SD produced by Amano Enzyme Inc. was used.

TABLE 2

| Formulation of Shampoo | | |
|---|---|---|
| Raw Material | Example 1-10 | Example 1-11 |
| Sodium polyoxyethylenelaurylethersulfate | 14 | 14 |
| Laurylsulfuric acid amidopropylbetaine | 4 | 4 |
| Coconut fatty acid diethanolamide | 3 | 3 |
| Cationized cellulose | 0.5 | 0.5 |
| Ethylene glycol distearate | 1 | 1 |
| Paraoxybenzoic acid ester | 0.2 | 0.2 |
| Compound of Example 1-4 | 0.3 | — |
| Compound of Example 1-5 | — | 0.3 |
| Deionized water | 77 | 77 |
| Total (% by mass) | 100 | 100 |

It could be confirmed that citronellal emits a fragrance when lipase is allowed to act on the hair after drying, which was obtained using the shampoo prepared in Example 1-10.

It could be confirmed that 2,6-dimethyl-5-heptenal emits a fragrance when lipase is allowed to act on the hair after drying, which was obtained using the shampoo prepared in Example 1-11.

Examples 1-12 and 1-13

Test for Confirming Fragrance Emission from Hair at the Time of Use of Hair Conditioner:

A hair conditioner was prepared according to a formulation shown in Table 3. A hair bundle of 10 cm in length was treated with the hair conditioner prepared and rinsed with tap water. After drying at room temperature for 15 hours, about 0.3 g of an aqueous 1% lipase preparation solution was sprayed onto the hair bundle, and the scent on the hair bundle was smelled to examine the presence or absence of fragrance emission from hair. As the lipase preparation, AY "Amano" 30SD produced by Amano Enzyme Inc. was used.

TABLE 3

| Formulation of Hair Conditioner | | |
|---|---|---|
| Raw Material | Example 1-12 | Example 1-13 |
| Stearyltrimethylammonium chloride | 0.5 | 0.5 |
| Distearyldimethylammonium chloride | 1.5 | 1.5 |
| Cetanol | 4.5 | 4.5 |
| Amino-modified silicone | 0.5 | 0.5 |
| Glycerin | 5 | 5 |
| Paraoxybenzoic acid ester | 0.2 | 0.2 |
| Compound of Example 1-4 | 0.3 | — |
| Compound of Example 1-5 | — | 0.3 |
| Deionized water | 87.5 | 87.5 |
| Total (% by mass) | 100 | 100 |

It could be confirmed that citronellal emits a fragrance when lipase is allowed to act on the hair after drying, which was obtained using the hair conditioner prepared in Example 1-12.

It could be confirmed that 2,6-dimethyl-5-heptenal emits a fragrance when lipase is allowed to act on the hair after drying, which was obtained using the hair conditioner prepared in Example 1-13.

Examples 1-14 and 1-15

Test for Confirming Fragrance Emission from Towel at the Time of Use of Liquid Detergent:

A liquid detergent was prepared according to a formulation shown in Table 4. A cotton towel was cleaned with the liquid detergent prepared and rinsed with tap water. After drying at room temperature for 15 hours, about 0.3 g of an aqueous 1% lipase preparation solution was sprayed onto the towel, and the scent on the towel was smelled to examine the presence or absence of fragrance emission from towel. As the lipase preparation, AY "Amano" 30SD produced by Amano Enzyme Inc. was used.

TABLE 4

| Formulation of Liquid Detergent | | |
|---|---|---|
| Raw material | Example 1-14 | Example 1-15 |
| Polyoxyethylene alkyl ether | 40 | 40 |
| Straight chain alkylbenzenesulfonate | 18 | 18 |
| Butyl carbitol | 10 | 10 |
| Propylene glycol | 3 | 3 |
| Monoethanolamine | 3 | 3 |

TABLE 4-continued

Formulation of Liquid Detergent

| Raw material | Example 1-14 | Example 1-15 |
|---|---|---|
| Compound of Example 1-4 | 0.5 | — |
| Compound of Example 1-5 | — | 0.5 |
| Deionized water | 25.5 | 25.5 |
| Total (% by mass) | 100 | 100 |

It could be confirmed that citronellal emits a fragrance when lipase is allowed to act on the towel after drying, which was obtained using the liquid detergent prepared in Example 1-14.

It could be confirmed that 2,6-dimethyl-5-heptenal emits a fragrance when lipase is allowed to act on the towel after drying, which was obtained using the liquid detergent prepared in Example 1-15.

Examples 1-16 and 1-17

Test for Confirming Fragrance Emission from Towel at the Time of Use of Softener:

A softener was prepared according to a formulation shown in Table 5. A cotton towel was treated with the softener prepared and rinsed with tap water. After drying at room temperature for 15 hours, about 0.3 g of an aqueous 1% lipase preparation solution was sprayed onto the towel, and the scent on the towel was smelled to examine the presence or absence of fragrance emission from towel. As the lipase preparation, AY "Amano" 30SD produced by Amano Enzyme Inc. was used.

TABLE 5

Formulation of Softener

| Raw Material | Example 1-16 | Example 1-17 |
|---|---|---|
| Tri(oxyethylene)methylammonium methylsulfate fatty acid ester | 18 | 18 |
| Polyoxyethylene(23) lauryl ether | 3 | 3 |
| Propylene glycol | 3 | 3 |
| Calcium chloride | 0.05 | 0.05 |
| Compound of Example 1-4 | 0.5 | — |
| Compound of Example 1-5 | — | 0.5 |
| Deionized water | 75.45 | 75.45 |
| Total (% by mass) | 100 | 100 |

It could be confirmed that citronellal emits a fragrance when lipase is allowed to act on the towel after drying, which was obtained using the softener prepared in Example 1-16.

It could be confirmed that 2,6-dimethyl-5-heptenal emits a fragrance when lipase is allowed to act on the towel after drying, which was obtained using the softener prepared in Example 1-17.

Examples 1-18 and 1-19 and Comparative Example 1-1

Flavor or Fragrance Composition:

A flavor or fragrance composition was prepared according to a formulation shown in Table 6.

TABLE 6

Formulation of Flavor or Fragrance Composition

| Raw material | Example 1-18 | Example 1-19 | Comparative Example 1-1 |
|---|---|---|---|
| Undecylene aldehyde | 5 | 5 | 5 |
| Allylamyl glycolate | 2 | 2 | 2 |
| Allyl enanthate | 5 | 5 | 5 |
| Benzyl acetate | 10 | 10 | 10 |
| Borneol | 6 | 6 | 6 |
| Cinnamic alcohol | 7 | 7 | 7 |
| Citronellol | 50 | 50 | 50 |
| Coumarin | 3 | 3 | 3 |
| Tricyclodecenyl acetate | 60 | 60 | 60 |
| α-Damascone | 1 | 1 | 1 |
| Dihydromyrcenol | 60 | 60 | 60 |
| Diphenyl oxide | 3 | 3 | 3 |
| Eucalyptus oil | 1 | 1 | 1 |
| Geraniol | 30 | 30 | 30 |
| Methyl dihydrojasmonate | 40 | 40 | 40 |
| Hexyl cinnamic aldehyde | 40 | 40 | 40 |
| Lime oil | 25 | 25 | 25 |
| Lemon oil | 30 | 30 | 30 |
| Linalol | 80 | 80 | 80 |
| Linalyl acetate | 40 | 40 | 40 |
| MUSK T (manufactured by Takasago International Corporation, registered trademark) | 100 | 100 | 100 |
| γ-Methylionone | 20 | 20 | 20 |
| Methyl nonyl ketone | 2 | 2 | 2 |
| Nerol | 20 | 20 | 20 |
| ORBITONE (manufactured by Takasago International Corporation, registered trademark) | 30 | 30 | 30 |
| 4-t-Butylcyclohexanol | 30 | 30 | 30 |
| p-t-Butylcyclohexyl acetate | 100 | 100 | 100 |
| Compound synthesized in Example 1-4 | 200 | — | — |
| Compound synthesized in Example 1-5 | — | 200 | — |
| Dipropylene glycol | — | — | 200 |
| Total (parts by mass) | 1000 | 1000 | 1000 |

Examples 1-20 to 1-23 and Comparative Examples 1-2 to 1-5

Lipase Detergent/Softener Combination Use Test:

A liquid detergent in which lipase is blended or not blended was prepared according to a formulation shown in Table 7. In addition, a softener was prepared according to a formulation shown in Table 8. As the lipase preparation, Lipex 100 L produced by Novozymes was used.

TABLE 7

Formulation of Liquid Detergent

| Raw Material | Blending of Lipase | Non-Blending of Lipase |
|---|---|---|
| Polyoxyethylene alkyl ether | 40 | 40 |
| Straight chain alkylbenzenesulfonate | 18 | 18 |
| Butyl carbitol | 10 | 10 |
| Propylene glycol | 3 | 3 |
| Monoethanolamine | 3 | 3 |
| Lipase preparation/Lipex 100L | 1 | — |
| Deionized water | 25 | 26 |
| Total (% by mass) | 100 | 100 |

TABLE 8

Formulation of Softener

| Raw material | Example 1-20 | Example 1-21 | Comparative Example 1-2 |
|---|---|---|---|
| Flavor or fragrance composition of Example 1-18 | 0.5 | — | — |
| Flavor or fragrance composition of Example 1-19 | — | 0.5 | — |
| Flavor or fragrance composition of Comparative Example 1-1 | — | — | 0.5 |
| Tri(oxyethylene)methylammonium methylsulfate fatty acid ester | 18 | 18 | 18 |
| Polyoxyethylene(23) lauryl ether | 3 | 3 | 3 |
| Propylene glycol | 3 | 3 | 3 |
| Calcium chloride | 0.05 | 0.05 | 0.05 |
| Citric acid | 0.01 | 0.01 | 0.01 |
| Sodium citrate | 0.1 | 0.1 | 0.1 |
| Deionized water | 75.34 | 75.34 | 75.34 |
| Total (% by mass) | 100 | 100 | 100 |

Subsequently, a cotton towel was cleaned with the liquid detergent obtained above, and the cotton towel after cleaning was dehydrated and then treated with the softener obtained above. After dehydration, the towel was dried overnight. The fragrance intensity and fresh feeling of the towel during drying and after drying were evaluated by ten expert panelists according to the following criteria. The evaluation score was determined by averaging the evaluated values of the expert panelists. The results are shown in Table 9.

(Evaluation Criteria of Fragrance Intensity)
0: Odorless
1: Barely perceptible odor
2: Weak odor can be seen in whether what of smell
3: Odor easily perceivable
4: Strong odor
5: Intense odor (Evaluation Criteria of Fresh Feeling)
0: No fresh feeling is sensed.
1: Fresh feeling is lightly sensed.
2: Fresh feeling is slightly sensed.
3: Fresh feeling is sensed.
4: Fresh feeling is fairly sensed.

TABLE 9

Fragrance Intensity and Fresh Feeling

| | | Example 1-22 | Comparative Example 1-3 | Example 1-23 | Comparative Example 1-4 | Comparative Example 1-5 |
|---|---|---|---|---|---|---|
| Liquid detergent | | blending of lipase | non-blending of lipase | blending of lipase | non-blending of lipase | blending of lipase |
| Softener | | Example 1-20 | Example 1-20 | Example 1-21 | Example 1-21 | Comparative Example 1-2 |
| Fragrance intensity | during drying | 3.3 | 2.8 | 3.1 | 2.8 | 2.6 |
| | after drying | 2.6 | 1.2 | 2.4 | 1.1 | 1 |
| Fresh feeling | during drying | 3.4 | 2.6 | 3.6 | 2.6 | 2.5 |
| | after drying | 2.8 | 0.6 | 3 | 0.7 | 0.5 |

It could be confirmed that when a softener using a compounded flavor or fragrance having blended therein a compound represented by formula (1) of the present invention and a detergent having blended therein lipase are used in combination, fragrance emission occurs and the fragrance intensity and fresh feeling after drying are enhanced.

Test Example 2

(Example 2-1) Synthesis of 2-isopropyl-5-methyl-1-cyclohexenyl Benzoate

[Chem. 24]

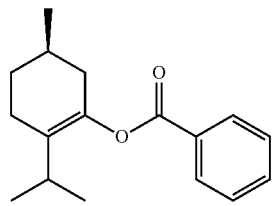

To a mixed solution of (−)-menthone 4.63 g (30 mmol) and benzoic anhydride 2.26 g (10 mmol), p-toluenesulfonic acid monohydrate 95 mg (0.5 mmol) was added at room temperature, followed by stirring at 100 to 110° C. (internal temperature) for 4.5 hours.

After cooling the reaction solution, the reaction was quenched by adding toluene and water. The reaction solution was extracted with toluene, and the organic layer was washed with a saturated sodium hydrogencarbonate aqueous solution and water. After drying the organic layer over sodium sulfate, the filtrate was concentrated under reduced pressure to obtain a crude product. The resulting crude product was purified by silica gel column chromatography to obtain 1.90 g of the target product.

(Example 2-2) Synthesis of 1,3-hexadienyl Benzoate

[Chem. 25]

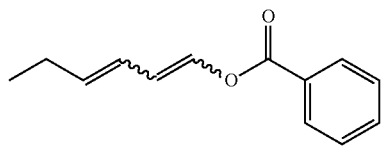

To a mixed solution of 2-hexenal 7.85 g (80 mmol), triethylamine 14.5 ml (104 mmol) and sodium benzoate 692 mg (4.8 mmol), benzoic anhydride 29.0 g (128 mmol) was added at room temperature, followed by stirring at 115 to 120° C. (internal temperature) for 8 hours.

After cooling the reaction solution, the reaction was quenched by adding toluene and water. The reaction solution was extracted with toluene, and the organic layer was washed with a saturated sodium hydrogencarbonate aqueous solution and water. After drying the organic layer over sodium sulfate, the filtrate was concentrated under reduced pressure to obtain a crude product. The resulting crude product was purified by silica gel column chromatography to obtain 13.26 g of the target product.

(Example 2-3) Synthesis of 3,7-dimethylocta-1,6-dienyl Benzoate

[Chem. 26]

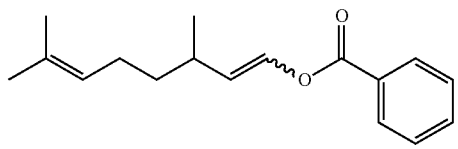

To a mixed solution of 1-citronellal 9.62 g (60 mmol), triethylamine 10.9 ml (78 mmol) and sodium benzoate 519 mg (3.6 mmol), benzoic anhydride 21.7 g (96 mmol) was added at room temperature, followed by stirring at 112 to 118° C. (internal temperature) for 10 hours.

After cooling the reaction solution, the reaction was quenched by adding toluene and water. The reaction solution was extracted with toluene, and the organic layer was washed with a saturated sodium hydrogencarbonate aqueous solution and water. After drying the organic layer over sodium sulfate, the filtrate was concentrated under reduced pressure to obtain a crude product. The resulting crude product was purified by silica gel column chromatography to obtain 9.38 g of the target product.

(Example 2-4) Synthesis of 2,6-dimethylhepta-1,5-dienyl Benzoate

[Chem. 27]

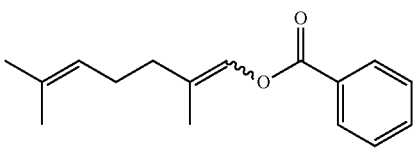

To a mixed solution of 2,6-dimethyl-5-heptenal 1.40 g (10 mmol), triethylamine 1.81 ml (13 mmol) and sodium benzoate 86 mg (0.6 mmol), benzoic anhydride 3.62 g (16 mmol) was added at room temperature, followed by stirring at 110 to 120° C. (internal temperature) for 10.5 hours.

After cooling the reaction solution, the reaction was quenched by adding toluene and water. The reaction solution was extracted with toluene, and the organic layer was washed with a saturated sodium hydrogencarbonate aqueous solution and water. After drying the organic layer over sodium sulfate, the filtrate was concentrated under reduced pressure to obtain a crude product. The resulting crude product was purified by silica gel column chromatography to obtain 1.85 g of the target product.

(Example 2-5) Synthesis of 3,5,5-trimethyl-1-hexenyl Benzoate

[Chem. 28]

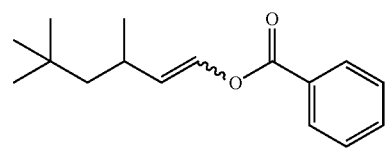

To a mixed solution of 3,5,5-trimethylhexanal 1.42 g (10 mmol), triethylamine 1.81 ml (13 mmol) and sodium benzoate 86 mg (0.6 mmol), benzoic anhydride 3.62 g (16 mmol) was added at room temperature, followed by stirring at 110 to 120° C. (internal temperature) for 7.5 hours.

After cooling the reaction solution, the reaction was quenched by adding toluene and water. The reaction solution was extracted with toluene, and the organic layer was washed with a saturated sodium hydrogencarbonate aqueous solution and water. After drying the organic layer over sodium sulfate, the filtrate was concentrated under reduced pressure to obtain a crude product. The resulting crude product was purified by silica gel column chromatography to obtain 0.56 g of the target product.

(Example 2-6) Synthesis of 1-octenyl Benzoate

[Chem. 29]

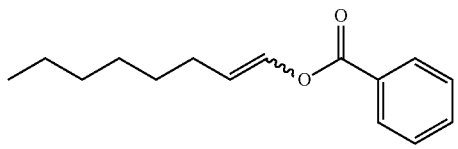

To a mixed solution of octanal 1.28 g (10 mmol), triethylamine 1.81 ml (13 mmol) and sodium benzoate 86 mg (0.6 mmol), benzoic anhydride 3.62 g (16 mmol) was added at room temperature, followed by stirring at 106 to 119° C. (internal temperature) for 9.5 hours.

After cooling the reaction solution, the reaction was quenched by adding toluene and water. The reaction solution was extracted with toluene, and the organic layer was washed with a saturated sodium hydrogencarbonate aqueous solution and water. After drying the organic layer over sodium sulfate, the filtrate was concentrated under reduced pressure to obtain a crude product. The resulting crude product was purified by silica gel column chromatography to obtain 2.01 g of the target product.

(Examples 2-7 to 2-17) Deodorizing Component Emission Test by Microorganism (Microorganism Culturing Method)
Culture of *Staphylococcus aureus* strain NBRC12732, *Staphylococcus epidermidis* strain JCM2414T, *Corynebacterium xerosis* strain JCM1324, *Pseudomonas aeruginosa* strain NBRC13275, *Bacillus subtilis* strain NBRC3134, and *Moraxella osloensis* strain ATCC19976:

After inoculating each of bacteria in Muller-Hinton liquid medium, shaking culture was performed at 30° C. for 20 hours. 3 mL of the resulting preculture solution was transferred to a vial bottle, and 10 mg of each of the compounds of Examples 2-2 to 2-6 was mixed, followed by hermetically sealing the bottle. Thereafter, shaking culture was further performed at 30° C. for 20 hours.
Culture of *Propionibacterium acnes* Strain JCM6473:

After inoculating bacteria in GAM bouillon liquid medium containing Hemin 0.5 ppm and Menadione 0.5 ppm, static culture was performed at 28° C. for 3 days under anaerobic conditions. 3 mL of the resulting preculture solution was transferred to a vial bottle, and 10 mg of each of the compounds of Examples 2-2 to 2-6 was mixed, followed by hermetically sealing the bottle. Thereafter, static culture was further performed at 28° C. for 3 days.
Culture of *Malassezia furfur* Strain NBRC0656:

After inoculating bacteria in Sabouraud liquid medium containing 0.1% Tween 80, static culture was performed at 28° C. for 3 days under anaerobic conditions. 3 mL of the resulting preculture solution was transferred to a vial bottle, and 10 mg of each of the compounds of Examples 2-2 to 2-6 was mixed, followed by hermetically sealing the bottle. Thereafter, static culture was further performed at 28° C. for 3 days.
(Test Method)
A peak area of the deodorizing compound was obtained by performing GC/MS analysis of the head space component contained in the vial bottle having 3 mL of microorganism culture solution in which 10 mg of each of the compound of Examples 2-2 to 2-6 was mixed. A microorganism culture solution having not mixed therein each of the compounds of Examples 2-2 to 2-6 was used as the control, and a peak area of the control was obtained by the same method as above.

The difference between the peak area of the deodorizing compound and the peak area of the control was calculated as the deodorizing component emission amount, and the results are shown in Tables 10 to 12.
(GC/MS Measurement Conditions)
Measuring apparatus: 7890GC/5975MSD (manufactured by Agilent Technologies)
Column: BC-WAX 50 m×0.25 mm I.D.
Temperature rise: 70° C.→220° C., 4° C./min
Split ratio: splitless

TABLE 10

Deodorizing Component Emission Amount When Mixed with *Staphylococcus aureus* NBRC12732 Culture Solution

| | Example 2-7 | Example 2-8 | Example 2-9 | Example 2-10 |
|---|---|---|---|---|
| | Compound | | | |
| | Compound of Example 2-3 | Compound of Example 2-4 | Compound of Example 2-5 | Compound of Example 2-6 |
| Deodorizing component | citronellal | 2,6-dimethyl-5-heptenal | trimethyl-hexanal | octanal |
| Deodorizing component emission amount | 1,064,240,572 | 132,554,000 | 189,916,125 | 129,928,279 |

It was confirmed from the results of Table 10 that the compound represented by formula (1) according to the present invention releases, as a deodorizing component, an aldehyde represented by formula (2) by the action of *Staphylococcus aureus*.

TABLE 11

Deodorizing Component Emission Amount by Various Microorganisms from Compounds of Examples 2-2 and 2-3

| | | Compound | |
|---|---|---|---|
| | Deodorizing component | Compound of Example 2-2 hexenal | Compound of Example 2-3 citronellal |
| Example 2-11 | *Staphylococcus epidermidis* JCM2414T | 17,179,106 | 76,886,509 |
| Example 2-12 | *Corynebacterium xerosis* JCM1324 | 15,168,728 | 692,091,257 |
| Example 2-13 | *Pseudomonas aeruginosa* NBRC13275 | 10,638,380 | 42,891,551 |
| Example 2-14 | *Bacillus subtilis* NBRC3134 | 106,596,512 | 66,939,425 |
| Example 2-15 | *Moraxella osloensis* ATCC19976 | 8,864,491 | 25,608,586 |
| Example 2-16 | *Propionibacterium acnes* JCM6473 | 3,265,759 | 15,450,553 |

It was confirmed from the results of Table 11 that the compound represented by formula (1) according to the present invention releases, as a deodorizing component, an aldehyde represented by formula (2) by the action of *Staphy-* lococcus epidermidis, Corynebacterium xerosis, Pseudomonas aeruginosa, Bacillus subtilis, Moraxella osloensis, or Propionibacterium acnes.

TABLE 12

Deodorizing Component Emission Amount When mixed with *Malassezia furfur* NBRC0656 Culture Solution

| Compound Deodorizing component | Compound of Example 2-5 trimethylhexanal |
|---|---|
| Example 2-17 *Malassezia furfur* | 19,153,037 |

It was confirmed from the results of Table 12 that the compound represented by formula (1) according to the present invention releases, as a deodorizing component, an aldehyde represented by formula (2) by the action of *Malassezia furfur*.

(Examples 2-18 and Comparative Example 2-1) Deodorization Test on Odor Emitted from Microorganisms (Test Method)

A gauze impregnated with Triolein 1 g, Tricaproin 1 g and Androsterone 0.5 g was set as a substrate in a petri dish of 33 mm in diameter $\phi$. Furthermore, 1 mL of *Staphylococcus aureus* test bacterial solution ($1\times10^9$ cfu/mL) previously prepared in 0.9% physiological saline containing 0.2% L-leucine as a substrate was mixed with 3.5 µL of the compound of Example 2-3, and the resulting mixture was uniformly impregnated into the gauze that was set. A cover was put on the petri dish and after hermetically sealing it, culture was performed at 37° C. for 20 hours. The level of odor comfort/discomfort of the gauze after culturing was sensorily evaluated by ten expert panelists according to the following criteria. The evaluation score was determined by averaging the evaluated values of the expert panelists.

In Comparative Example 2-1, evaluation was made on gauze subjected to the same culturing without mixing the compound of Example 2-3. The results are shown in Table 13.

It is known that each of Triolein, Tricaproin, Androsterone and L-leucine emits malodor by the action of microorganisms.

(Evaluation Criteria of Level of Comfort/Discomfort)
+4: Extreme comfort
+3: great comfort
+2: comfort
+1: slight comfort
0: neither comfort nor discomfort
−1: slight discomfort
−2: discomfort
−3: great discomfort
−4: extreme discomfort

TABLE 13

|  | Example 2-18 | Comparative Example 2-1 |
|---|---|---|
| Level of comfort/discomfort | 1.5 | −3.2 |

It was confirmed from the results of Table 13 that as shown by Comparative Example 2-1, malodor was emitted along with proliferation of *Staphylococcus aureus* under the test conditions above and the compound represented by formula (1) can mitigate the malodor caused by *Staphylococcus aureus*.

Examples 2-19 and 2-20

A deodorizing mist was prepared according to a formulation shown in Table 14.

TABLE 14

Formulation of Deodorizing Mist

| Raw Material | Example 2-19 | Example 2-20 |
|---|---|---|
| Compound of Example 2-1 | 1 | — |
| Compound of Example 2-3 | — | 1 |
| Polyoxyethylene(60) hydrogenated caster oil | 3 | 3 |
| Deionized water | 96 | 96 |
| Total (% by mass) | 100 | 100 |

(Examples 2-21 and 2-22 and Comparative Examples 2-2 and 2-3) Deodorization Test on Worn Sock Odor by Deodorizing Mist (Test Method)

A cleaned right-foot sock made of man-made fiber was sprayed with 0.6 g of each of deodorizing mists obtained in Examples 2-19 and 2-20. In Comparative Examples, a cleaned left-foot sock made of man-made fiber, which was not sprayed with deodorizing mist, was used. The level of odor comfort/discomfort of the sock before wearing as well as after wearing for 15 hours was sensorily evaluated by ten expert panelists according to criteria. As for the criteria, the criteria of Example 2-18 was used. The evaluation score was determined by averaging the evaluated values of the expert panelists. The results are shown in Table 15.

TABLE 15

| Sock | | Example 2-21 (sprayed with deodorizing mist obtained in Example 2-19) right foot | Comparative Example 2-2 left foot | Example 2-22 (sprayed with deodorizing mist obtained in Example 2-20) right foot | Comparative Example 2-3 left foot |
|---|---|---|---|---|---|
| Level of comfort/discomfort | before wearing | 0 | 0 | 0 | 0 |
|  | after wearing 15 hours | 1.8 | −2.2 | 1.5 | −2 |

In both of Example and Comparative Example, the sock before wearing was substantially odorless. The sock of Comparative Example after wearing for 15 hours, which was not sprayed with the deodorizing mist of the present invention, emitted odor and caused discomfort, but in the stock of Example after wearing for 15 hours, which was sprayed with the deodorizing mist of the present invention, offensive odor was not sensed. It could be confirmed that a deodorizing component is released from the compound represented by formula (1) and the unpleasant sensation is thereby alleviated.

Example 2-23

A deodorizing spray was prepared according to a formulation shown in Table 16.

TABLE 16

Formulation of Deodorizing Spray

| Raw Material | Example 2-23 |
|---|---|
| Compound of Example 2-4 | 0.5 |
| Ethanol | 19.5 |
| LPG | 80 |
| Total (% by mass) | 100 |

(Example 2-24 and Comparative Example 2-4) Deodorization Test on Sweat Shirt by Deodorizing Spray (Test Method)

A sweaty shirt was prepared by wearing a cleaned cotton shirt and exercising vigorously. The shirt was put in a plastic bag and left standing at room temperature for 12 hours in a hermetically sealed state. After taking out the shirt from the plastic bag, 1 g of the deodorizing spray obtained in Example 2-23 was sprayed onto the right-side portion of the shirt. In Comparative Example, the deodorizing spray was not sprayed onto the left-side portion of the shirt. Thereafter, the shirt was left standing for 3 hours. The level of odor comfort/discomfort in the right-side portion and left-side portion of the shirt was sensorily evaluated by ten expert panelists according to criteria. As for the criteria, the criteria of Example 2-18 was used. The evaluation score was determined by averaging the evaluated values of the expert panelists. The results are shown in Table 17.

TABLE 17

| | Example 2-24 | Comparative Example 2-4 |
|---|---|---|
| Level of comfort/discomfort | 1.4 | −2.8 |

The left-side portion of the shirt not sprayed with the deodorizing spray of the present invention emitted odor and caused discomfort, but in the right-side portion of the shirt sprayed with the deodorizing spray of the present invention, offensive odor was not sensed. It could be confirmed that a deodorizing component is released from the compound represented by formula (1) and the unpleasant sensation is thereby alleviated.

(Examples 2-25 to 2-27) Application Example to Deodorizing Liquid Detergent

A deodorizing liquid detergent was prepared according to a formulation shown in Table 18.

TABLE 18

Formulation of Deodorizing Liquid Detergent

| Raw Material | Example 2-25 | Example 2-26 | Example 2-27 |
|---|---|---|---|
| Polyoxyethylene alkyl ether | 40 | 40 | 38 |
| Straight chain alkylbenzenesulfonate | 18 | 18 | 18 |
| Butyl carbitol | 3 | 3 | 2 |
| Propylene glycol | 3 | 3 | 4 |
| Monoethanolamine | 3 | 3 | 3 |
| Flavor or fragrance | 0.5 | 0.5 | 0.4 |
| Compound of Example 2-4 | 0.5 | — | 0.3 |
| Compound of Example 2-6 | — | 0.4 | 0.3 |
| Deionized water | 32 | 32.1 | 34 |
| Total (% by mass) | 100 | 100 | 100 |

(Examples 2-28 to 2-30) Application Example to Deodorizing Softener

A deodorizing softener was prepared according to a formulation shown in Table 19.

TABLE 19

Formulation of Deodorizing Softener

| Raw material | Example 2-28 | Example 2-29 | Example 2-30 |
|---|---|---|---|
| Tri(oxyethylene)methylammonium methylsulfate fatty acid ester | 18 | 18 | 17 |
| Polyoxyethylene(23) lauryl ether | 3 | 3.5 | 4 |
| Propylene glycol | 3 | 3 | 2 |
| Calcium chloride | 0.05 | 0.05 | 0.05 |
| flavor or fragrance | 0.8 | 1 | 0.8 |
| Compound of Example 2-2 | 0.3 | — | 0.3 |
| Compound of Example 2-5 | — | 0.4 | 0.3 |
| Deionized water | 74.85 | 74.05 | 75.55 |
| Total (% by mass) | 100 | 100 | 100 |

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2017-007930) filed on Jan. 19, 2017 and Japanese Patent Application (Patent Application No. 2017-058118) filed on Mar. 23, 2017, the contents of which are incorporated herein by way of reference.

INDUSTRIAL APPLICABILITY

Since the compound represented by formula (1) can release an aldehyde or ketone that is a fragrance component by the action of a hydrolysate, the compound can be used as a flavor or fragrance precursor and is useful.

By blending the compound represented by formula (1) according to the present invention in a flavor or fragrance composition or a product of every sort, the lingering fragrance having fresh feeling can be caused to last on the clothing, hair or skin, and the compound has applicability in the flavor or fragrance industry.

The invention claimed is:

1. A compound of Formula (4):

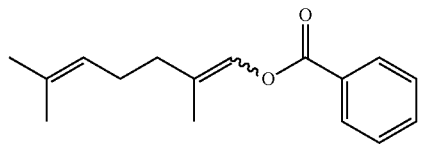

Formula (4)

wherein in Formula (4), a wavy line represents either one of E and Z geometric isomers or a mixture thereof.

2. A flavor or fragrance composition containing the compound according to claim 1.

3. An aroma product, a laundry care product, a hair care product, a cosmetic, a cleaner or a deodorant, containing the compound according to claim 1.

* * * * *